(12) United States Patent
Erwin, III et al.

(10) Patent No.: US 10,254,293 B2
(45) Date of Patent: Apr. 9, 2019

(54) **SENSITIVE AND SPECIFIC ASSAY FOR *BABESIA* SPP**

(71) Applicant: Immunetics, Inc., Marlborough, MA (US)

(72) Inventors: James L. Erwin, III, Hingham, MA (US); Neil X. Krueger, Roslindale, MA (US); Andrew E. Levin, Wellesley, MA (US)

(73) Assignee: IMMUNETICS, INC., Marlborough, MA (US)

( * ) Notice: Subject to any disclaimer, the term of this patent is extended or adjusted under 35 U.S.C. 154(b) by 0 days.

(21) Appl. No.: 13/657,394

(22) Filed: Oct. 22, 2012

(65) Prior Publication Data
US 2013/0244258 A1     Sep. 19, 2013

Related U.S. Application Data

(60) Provisional application No. 61/549,612, filed on Oct. 20, 2011.

(51) Int. Cl.
*G01N 33/68*     (2006.01)
*G01N 33/569*     (2006.01)

(52) U.S. Cl.
CPC ... *G01N 33/6893* (2013.01); *G01N 33/56905* (2013.01); *G01N 2333/44* (2013.01)

(58) Field of Classification Search
None
See application file for complete search history.

(56) References Cited

U.S. PATENT DOCUMENTS

| | | | |
|---|---|---|---|
| 5,273,884 A | 12/1993 | Gale et al. | |
| 6,183,976 B1 | 2/2001 | Reed et al. | |
| 6,214,971 B1 | 4/2001 | Reed et al. | |
| 6,306,396 B1 | 10/2001 | Reed et al. | |
| 6,451,315 B1 | 9/2002 | Reed et al. | |
| 6,569,433 B1 | 5/2003 | Reed et al. | |
| 2004/0023865 A1 | 2/2004 | Reed et al. | |
| 2005/0003459 A1* | 1/2005 | Krutzik | 435/7.9 |

FOREIGN PATENT DOCUMENTS

| | | |
|---|---|---|
| WO | WO-9011776 A1 | 10/1990 |
| WO | WO-2006031544 A2 | 3/2006 |
| WO | WO-2013/059795 A1 | 4/2013 |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000,10:398-400).*
Homer, M. J., et al. "A Polymorphic Multigene Family Encoding an Immunodominant Protein from *Babesia microti*," Journal of Clinical Microbiology, 38(1): 362-368 (Jan. 2000).
Homer, Mary J., et al. "Identification and Characterization of Putative Secreted Antigens from *Babesia microti*," Journal of Clinical Microbiology, 41(2): 723-729 (Feb. 2003).
Houghton, Raymond L., et al. "Identification of *Babesia microti*-specific immunodominant epitopes and development of a peptide EIA for detection of antibodies in serum," Transfusion, 42: 1488-1496 (Nov. 2002).
Lodes, Michael J., et al. "Serological Expression Cloning of Novel Immunoreactive Antigens of *Babesia microti*," Infection and Immunity, 68(5): 2783-2790 (May 2000).
Priest, Jeffrey W., et al. "Multiplex Assay Detection of Immunoglobulin G Antibodies That Recognize Babesia microti Antigens," Clinical and Vaccine Immunology, 19(9): 1539-1548 (2012).
International Search Report and Written Opinion for PCT/US2012/061333 dated Mar. 29, 2013.
Asad, S. et al., Transfusion-transmitted babesiosis in Rhode Island, Transfusion, 49(12):2564-2573 (2009).
Chisholm, E.S. et al., Babesia microti infection in man: evaluation of an indirect immunofluorescent antibody test, Am. J Trap. Med. Hyg., 27(1 Pt 1):14-19 (1978).
Erwin, J.L. et al., Development of a sensitive and specific ELISA for antibodies to Babesia microti in human serum, AABB Meeting, (2011).
Gubernot, D.M. et al., Babesia infection through blood transfusions: reports received by the US Food and Drug Administration, 1997-2007, Clin. Infect Dis., 48(1): 25-30 (2009).
Herwaldt, B.L. et al., Transfusion-associated babesiosis in the United States: a description of cases, Ann. Intern Med, 155(8): 509-19 (2011).
Krause, P.J. et al., Diagnosis of babesiosis: evaluation of a serologic test for the detection of Babesia microti antibody, J Infect. Dis., 169(4):923-926 (1994).
Leiby, D.A., Babesiosis and blood transfusion: flying under the radar, Vox Sang, 90(3): 1571-65 (2006).
Leiby, D.L. et al., Transfusion-transmitted Babesia spp.: bull's-eye on Babesia microti, Clin. Micro. Reviews, 24(1): 14-28 (2011).
Leiby, D.L., Transfusion-associated babesiosis: shouldn't we be ticked off?, Annals Int. Med., 155(8): 556-7 (2011).
Loa, C.C. et al., Serological diagnosis of human babesiosis by IgG enzyme-linked immunosorbent assay, Curr. Method, 49: 385-389 (2004).

(Continued)

*Primary Examiner* — Robert A Zeman
(74) *Attorney, Agent, or Firm* — Choate Hall & Stewart LLC; Charles E. Lyon; Brian E. Reese

(57) ABSTRACT

The invention is directed to methods of using novel *Babesia* antigen peptides in detecting *Babesia* spp. in a sample. The methods may be adapted to assays suitable for high blood volume screening, use for clinical diagnosis of patients with babesiosis, or assaying blood contaminated with *Babesia* spp., such as *B. microti*.

21 Claims, 7 Drawing Sheets
Specification includes a Sequence Listing.

(56) References Cited

OTHER PUBLICATIONS

Luo, Y., et al., Identification and characterization of a novel secreted antigen 1 of Babesia microti and evaluation of its potential use in enzyme-linked immunosorbent assay and immunochromatographic test, Parasitol. Int., 60(2): 119-125 (2011).

Pantanowitz, L. et al. Extracellular Babesia microti parasites, Transfusion, 41(4): 440 (2001).

* cited by examiner

Figure 4

SENSITIVE AND SPECIFIC ASSAY FOR *BABESIA* SPP

RELATED APPLICATIONS

This application claims benefit under 35 U.S.C. § 119(e) of U.S. Provisional Patent Application No. 61/549,612 filed Oct. 20, 2011.

SEQUENCE LISTING

The instant application contains a Sequence Listing which has been submitted in ASCII format via EFS-Web and is hereby incorporated by reference in its entirety. Said ASCII copy, created on May 20, 2013, is named IMA-032.01_SL.txt and is 20,942 bytes in size.

BACKGROUND OF THE INVENTION

Human babesiosis is a malaria-like illness caused by infection of red blood cells by various species of protozoan parasites of the genus *Babesia*. *B. microti* is responsible for most human infections reported in the United States, and this parasite is endemic in parts of the Northeast and upper Midwest. *B. microti* infections are asymptomatic in most individuals but can lead to severe illness or death, especially in immunosuppressed, asplenic or elderly individuals. The parasite is primarily transmitted to humans by exposure to deer ticks in endemic areas. However, babesiosis can also be transmitted by blood transfusion. The parasite is able to tolerate standard blood banking conditions and adjunct processing procedures (Leiby D A. *Vox Sang* 2006, 90: 157-165) as evidenced by transmission following transfusion of a whole blood, liquid-stored and frozen-deglycerolized red cells, as well as whole blood derived platelets (Pantanowitz L, et al. *Transfusion* 2001, 41: 440). Over 100 cases of transfusion-transmitted babesiosis (TTB) have been reported to the FDA since 1979 and at least 12 fatalities since 2005 (Gubernot D M, et al. *Clin Infect Dis* 2009, 48: 25-30). Despite being acknowledged as the foremost unaddressed infectious risk to the U.S. blood supply, there is an urgent and unmet need for blood donor screening to be implemented (Herwaldt B L, et al. *Ann Intern Med* 2011, September, 2011:155 (5)). Furthermore, with no assay licensed for blood screening and no donor screening strategy in widespread use, TTB continues to pose risk to transfusion recipients in the US.

Blood donations from *Babesia*-endemic areas in the U.S. can exhibit up to 1% seropositivity for *B. microti*, and the distribution of *Babesia* seropositivity is spreading rapidly to adjacent states and elsewhere. Indeed, the *B. microti* species of *Babesia* parasite, hitherto rare in Europe, has been reported in localized regions of Germany and Switzerland, with human seroprevalence between 1% and 9% (Leiby D L et al. *Clin Micro Reviews* 2011, Jan., 24 (1): 14-28).

Babesiosis has a wide spectrum of clinical presentation that is largely governed by immune status of the host. While the majority of naturally acquired infections are either asymptomatic or mild and self-limiting in the immunocompetent host, infection at extremes of age, in the immunocompromised and/or in individuals with asplenia has a high risk of severe complicated and even fatal disease (Asad S, et al. *Transfusion* 2009, 49:12, 2564-2573). Transfusion recipients share notable overlap with these high-risk groups and TTB confers an estimated mortality of 5-9%.

The emerging threat of human babesiosis as a transfusion-transmitted disease has led to a consensus by the Food and Drug Administration (FDA) and the American Association of Blood Banks (AABB) that screening of blood donations for *Babesia* is urgently required for blood safety (Leiby D L, *Annals Int Med* 2011, August, 155). Recent reports showing an alarming increase in transfusion-transmitted babesiosis (TTB), which can cause serious illness or death in immunocompromised patients, underscore this need. Therefore a quick, easy, and sensitive assay for blood screening and detecting *Babesia* is needed, and as such would facilitate a ready supply of blood that are free of *Babesia* contamination and safe for use by humans.

Currently no commercial, validated and FDA approved test is available for this pathogen. *B. microti* is currently detectable by four principal assay methods: microscopic observation of Giemsa-stained blood smears, indirect immunofluorescence (IFA), PCR or xenodiagnosis by hamster inoculation. The assay performances reported for these methods are compared in Table 1. The IFA method, originally described over 30 years ago (Chisholm E S, et al, *Am. J. Trop. Med. Hyg.* 1978; 27:14-19; Krause P J, et al. *Antibody, J. Infect. Dis.* 1994; 169:923-926), remains the only currently available serological method. IFA requires microscopy skills, specific training and access to a fluorescence microscope, which is practical for some reference laboratories, but not a technique amenable to routine use and practice by non-specialists. Examination of thin blood smears for piroplasms similarly requires a microscope and skilled operator and is subject to the same limitations (Leiby D A. *Vox Sang* 2006, 90: 157-165.). PCR demands a highly controlled environment to avoid contamination and artifactual results, complex and expensive instrumentation and reagents, and a high degree of training to perform properly. Table 1: Comparative performances between *Babesia* current tests from Chisholm E S et al. *Am. J. Trop. Med. Hyg.* 1978; 27:14-19 and Krause P J et al. *Antibody, J. Infect. Dis.* 1994; 169:923-926.

TABLE 1

|  | Sensitivity | Specificity | PPV | NPV |
|---|---|---|---|---|
| Blood smear | 84% | 100% | 100% | 62% |
| IFA | 88%-96% | 90%-100% | 69%-100% | 96%-99% |
| PCR | 95% | 100% | 100% | 83% |
| Xenodiagnosis | 74% | 100% | 100% | 50% |

SUMMARY OF THE INVENTION

In contrast, compared to other available methods of detection such as culture, the assays and methods described herein requires no specific training beyond pipetting skills, does not require equipment more sophisticated or costly than pipettors and a microplate reader, is suitable for either low or higher volume testing using existing microplate-based instrumentation or automation which is found in many clinical laboratories, and is easily scalable for large scale production.

In one aspect, the invention feature methods for identifying *Babesia* spp. in a sample, the method comprising:
(a) contacting the sample to a solid support immobilized with at least one *Babesia* antigen peptide selected from the group consisting of a polypeptide comprising an amino acid sequence which is at least 80% identical to the amino acid sequence of SEQ ID NO: 39, 40, 41, or 42;
(b) contacting the product of step (a) with a detectable label linked to a reagent that binds to the captured antibody at a different epitope than the epitope to which (a) binds;

(c) contacting the product of (b) with a substrate under appropriate conditions and for an appropriate amount of time, thereby forming a colored-reaction product; and (d) detecting the formation of the colored-reaction product as an indication of the presence of *Babesia* spp. in the sample.

In certain embodiments, the method further comprises a wash step after step (a).

In certain embodiments, the *Babesia* spp. is selected from the group consisting of *Babesia bigemina, Babesia bovis, Babesia canis, Babesia cati, Babesia divergens, Babesia duncani, Babesia felis, Babesia gibsoni, Babesia herpailuri, Babesia jakimovi, Babesia major, Babesia microti, Babesia ovate,* and *Babesia pantherae.*

In certain embodiments, the *Babesia* spp. is *Babesia microti*.

In certain embodiments, the sample is blood or a blood product.

In another aspect, the invention relates to diagnostic kits for the identification of *Babesia* spp. in a sample, the kit comprising at least one *Babesia* antigen peptide selected from the group consisting of SEQ ID NO: 39, SEQ ID NO: 40, SEQ ID NO: 41, SEQ ID NO: 42, or combination thereof.

In certain embodiments, the diagnostic kit comprises a *Babesia* antigen peptide affixed to a solid support.

In another aspect, the invention relates to an isolated *Babesia* antigen peptide selected from the group consisting of: a) a polypeptide comprising an amino acid sequence which is at least 80% identical to the amino acid sequence of SEQ ID NO: 38, 39, 40, 41, or 42; or b) a polypeptide comprising an amino acid sequence of SEQ ID NO: 38, 39, 40, 41, or 42.

In another aspect, the invention relates to a composition comprising at least one isolated *Babesia* antigen peptide selected from the group consisting of:

a) a polypeptide comprising an amino acid sequence which is at least 80% identical to the amino acid sequence of SEQ ID NO: 38, 39, 40, 41, 42, or combination thereof; or b) a polypeptide comprising an amino acid sequence of SEQ ID NO: 38, 39, 40, 41, 42, or combination thereof.

The detection assay described herein does not require sophisticated instrumentation. In one aspect of the invention, the detection assay described presents a rapid and cost-effective approach to screening blood donors and blood products for *Babesia* spp., such as *B. microti* contamination. Further, in yet another aspect of the invention, the detection assay can be used to support the clinical diagnosis of babesiosis. In one embodiment, the colored reaction product may be read visually. In another embodiment, the colored reaction product may be read using a spectrophotometer or an ELISA reader. The detection assay, described herein, provides a positive or negative reading of *Babesia* contamination.

The features and benefits of the assay include a sensitivity-detection of *Babesia* at a sensitivity of 100% versus IFAT, sensitivity for seropositive babesiosis cases of 100%, specificity with normal donor sera from a non-endemic area of ≥99%, and a short assay time and the option of immediate readout using visual evaluation. The flexible format and simplicity of the assay lends itself easily to laboratory automation for batch testing in the blood bank or point of use, e.g. testing in the hospital, doctor's office, manufacturing plant, or in the field (depending of course on the sample to be evaluated). Thus, the *Babesia* detection assay format is simple and straightforward.

Other Features and advantages of the invention will become apparent based on the following Detailed Description and Claims.

BRIEF DESCRIPTION OF THE DRAWINGS

FIG. 4 shows the result of a Western blot of *B. microti* and *B. divergens*/MO1 patient sera. Patient sera from the Upper Midwest and New England detect proteins that are (1) unique to the parasite lysate and (2) not reactive with normal human serum. Bands (p 36-37) may relate to BMN1-9 by virtue of its co-migration with the band detected on the same lysate with a monoclonal antibody specific for BMN1-9 (provided by Dr. Jeffrey Priest, CDC). The reactivity of an MO-1 (*B. divergens*) patient serum with individual bands in the *B. microti* lysate suggests that further characterization of antigens may yield a more pan-reactive serodiagnostic assay.

DETAILED DESCRIPTION OF THE INVENTION

I. Definitions

Figure 1:
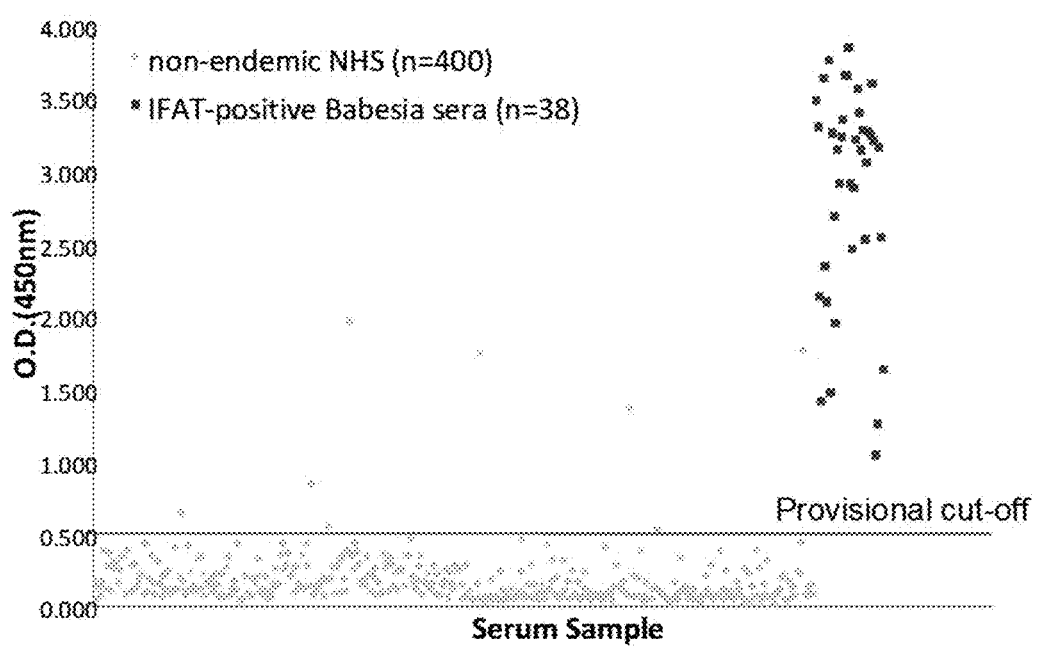
FIG. 1 is a graph depicting the distribution of absorbances for samples tested in an assay containing all 4 *Babesia* antigen peptides, BMN1-17A, BMN1-17B, BMN1-9A, and BMN1-9B, combined. The confirmed *Babesia*-positive samples show absorbances greater than 1.0 for at least one of the 4 peptides. In contrast, the majority of control samples (from non-endemic areas) show absorbances less than 0.1, and, except for eight samples, less than 0.53 OD; thus, a provisional cutoff of 0.53 would yield a specificity of 98%. Among donors in an area endemic for the parasite, a specificity of 95% was still observed with the same cutoff.

For convenience, certain terms employed in the specification, examples, and appended claims are provided. Unless defined otherwise, all technical and scientific terms used herein have the same meaning as commonly understood by one of ordinary skill in the art to which this invention belongs.

"Amino acid" is used herein to refer to either natural or synthetic amino acids, including glycine and D or L optical isomers, and amino acid analogs and peptidomimetics.

"Antibody" is used herein to refer to binding molecules including immunoglobulin molecules and immunologically active portions of immunoglobulin molecules, i.e., molecules that contain an antigen-binding site. Immunoglobulin molecules useful in the invention can be of any class (e.g., IgG, IgE, IgM, IgD, and IgA) or subclass. Native antibodies and immunoglobulins are usually heterotetrameric glycoproteins of about 150,000 daltons, composed of two identical light chains and two identical heavy chains. Each heavy chain has at one end a variable domain followed by a number of constant domains. Each light chain has a variable domain at one end and a constant domain at its other end. Antibodies include, but are not limited to, polyclonal, monoclonal, bispecific, chimeric, partially or fully humanized antibodies, fully human antibodies (i.e., generated in a transgenic mouse expressing human immunoglobulin genes), camel antibodies, and anti-idiotypic antibodies. An antibody, or generally any molecule, "binds specifically" to an antigen (or other molecule) if the antibody binds preferentially to the antigen, and, e.g., has less than about 30%, preferably 20%, 10%, or 1% cross-reactivity with another molecule. The terms "antibody" and "immunoglobulin" are used interchangeably.

"Babesia" refers to infectious protozoan species of the Babesia family, including, inter-alia: Babesia bigemina, Babesia bovis, Babesia canis, Babesia cati, Babesia divergens, Babesia duncani, Babesia felis, Babesia gibsoni, Babesia herpailuri, Babesia jakimovi, Babesia major, Babesia microti, Babesia ovate, and Babesia pantherae.

"Babesia antigen peptide" is used herein to refer to a peptide sequence derived from clones of the Babesia BMN1 family, including, but not limited to, BM4, MN-10, BMN1-3B, BMN1-9, BMN1-10, BMN1-11, BMN1-8, MN-10, BMN1-4, BMN1-15, BMN1-7, BMN1-5, BMN1-6, BMN1-12, BMN1-2, BMN1-13, BMN1-3, BMN1-17, BMN1-20, and BMN1-21. The Babesia antigen peptides retain biological activity, e.g., the ability to bind anti-Babesia antibodies. The Babesia antigen peptides can be isolated from native sequences, synthesized by methods known in the art, chemically modified, or conjugated to a polymer and/or capture reagent.

"Bind" or "binding" are used herein to refer to detectable relationships or associations (e.g. biochemical interactions) between molecules.

"Capture reagent" refers to a substance, which interacts with (e.g. covalently binds) a Babesia peptide antigen, or chemically modified form thereof, i.e., two different molecules wherein one of the molecules binds with the second molecule through chemical and/or physical means. The two molecules are related in the sense that their binding with each other is such that they are capable of distinguishing their binding partner from other assay constituents having similar characteristics. The members of the binding pair can be referred to as ligand and receptor (antiligand), a binding pair member and binding pair partner, and the like. Examples include without limitation, antigen and antibody binding pair members, biotin and avidin, carbohydrates and lectins, complementary nucleotide sequences, complementary peptide sequences, effector and receptor molecules, enzyme cofactors and enzymes, enzyme inhibitors and enzymes, bovine serum albumin and the like, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogues of the original specific binding member.

"Consensus sequence" is used herein to refer to the sequence formed from the most frequently occurring amino acids (or nucleotides) in a family of related sequences (See. e.g., Winnaker, *From Genes to Clones,* 1987). In a family of proteins, each position in the consensus sequence is occupied by the amino acid occurring most frequently at that position in the family. If two amino acids occur equally frequently, either can be included in the consensus sequence.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Mutations can be introduced randomly along all or part of a natural coding sequence, such as by saturation mutagenesis, and the resultant mutants can be screened for biological activity.

"Detectable label" is used herein to refer to a molecule capable of detection, including, but not limited to, radioactive isotopes, fluorophores, chemiluminescent moieties, enzymes, enzyme substrates, enzyme cofactors, enzyme inhibitors, dyes, metal ions, and the like. "Fluorophore" refers to a substance or a portion thereof which is capable of exhibiting fluorescence in the detectable range. Particular examples of labels which may be used include fluorescein, rhodamine, dansyl, umbelliferone, Texas red, luminol, NADPH, beta-galactosidase, and horseradish peroxidase.

"Nucleic acid" is used herein to refer to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

"Peptide" is used herein to refer to a polymer of amino acids of relatively short length (e.g. less than 50 amino acids). The polymer may be linear or branched, it may comprise modified amino acids, and it may be interrupted by non-amino acids. The term also encompasses an amino acid polymer that has been modified; for example, by disulfide bond formation, glycosylation, lipidation, acetylation, phosphorylation, or any other manipulation, such as conjugation with a labeling component.

"Sample" refers to a mixture. Examples include saliva, urine, hydration fluid, nutrient fluid, blood, blood product, plasma, serum, cerebrospinal fluid (CSF), tissue extract, dialysis fluid, serum, plasma, interstitial fluid, sputum, ocular lens liquid, sweat, milk, synovial liquid, peritoneal liquid, transdermal exudates, pharyngeal exudates, bronchoalveolar lavage, tracheal aspirations, semen, cervical mucus, vaginal or urethral secretions, amniotic liquid, cell, tissue, organ or portions thereof obtained from a subject, such as human, animal, mammal, insect, reptile, and the like.

"Solid support" refers to porous or non-porous support for immobilizing reagents. Examples include membranes (i.e., test strips, dip strips, immunochromatographic strip, dip sticks, Western blots, wicks, Southern blots, Northern blots, dot-blots), pads (i.e., made from CF7 Whatman paper), microarrays, slides, film, and microplates. Solid supports may be comprised of various materials, including polyethylene, nylon, natural macromolecules, polyvinyl sulfone, silica, glass fiber, glass fiber with binder, cellulose acetate, and nitrocellulose (NC).

"Specifically binds" is used herein to refer to the interaction between two molecules to form a complex that is relatively stable under physiologic conditions. The term is used herein in reference to various molecules, including, for example, the interaction of an antibody and an antigen (e.g. a peptide). Specific binding can be characterized by a dissociation constant of at least about $1\times10^{-6}$ M, generally at least about $1\times10^{-7}$ M, usually at least about $1\times10^{-8}$ M, and particularly at least about $1\times10^{-9}$ M or $1\times10^{-10}$ M or greater. Methods for determining whether two molecules specifically bind are well known and include, for example, equilibrium dialysis, surface plasmon resonance, and the like.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences and the percent homology between two sequences is a function of the number of conserved positions shared by the sequences, taking into account the number of gaps, and the length of each gap, which need to be introduced for optimal alignment of the two sequences. The comparison of sequences and determination of percent identity and/or homology between two sequences can be accomplished using a mathematical algorithm. In certain embodiments, the percent identity between two amino acid sequences is determined using the Needleman and Wunsch ((1970) *J. Mol. Biol.* 48:444-453) algorithm which has been incorporated into the GAP program in the GCG software package (available on the world wide web with the extension gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available on the world wide web with the extension gcg.com), using a NWSgapdna CMP matrix and a gap weight of 40, 50, 60, 70; or 80 and a length weight of 1, 2, 3, 4, 5, or 6. A particularly set of parameters (and the one that should be used unless otherwise specified) cab be a Blossum 62 scoring matrix with a gap penalty of 12, a gap extend penalty of 4, and a frame shift gap penalty of 5.

The percent identity and/or homology between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

II. *Babesia* Antigen Peptides

Described herein are highly specific peptides that can bind to antibodies to certain *Bambesia* antigens. Such novel *Babesia* antigen peptides were developed based, in part, on a selection of immunodominant antigens from *B. microti* identified originally by expression cloning described in Homer et al. (Homer M J, et al. *J. Clin. Microbiol.* 2003 February; 41(2):723-729). The strategy consisted of expression of open reading frames (ORFs) by bacteriophage display and identification of antigen candidates by reaction with pooled sera from patients diagnosed with babesiosis. Sera from chronically infected SCID mice were subsequently used to select for antigens likely to be shed by the parasite (Lodes M J, et al. *Infect Immun.* 2000 May; 68(5): 2783-2790). Two antigens, designated BMN1-17 and MN-10, were identified which had high reactivity with babesiosis patient sera and low reactivity with normal donors (U.S. Pat. Nos. 6,569,433B1; 6,451,315B1; 6,306, 396B1; 6,214,971B1 and 6,183,976B1). Recombinant proteins corresponding to BMN1-17 and MN-10 were synthesized. A partial clone of BMN1-17 and a second antigen, BMN1-9, which was related to MN-10 by BLAST analysis, were obtained. BMN1-9 had been previously identified by Luo et al. (Luo Y, et al. *Parasitol. Int.* 2011; June; 60(2): 119-125), who reported that reactivity against BMN1-9 occurred within a week post-infection in experimental animals, and persisted for many months. For this reason, BMN1-9 was chosen as a candidate antigen for detection of sero-reactivity.

Loa et al. reported the identification of potentially dominant epitopes from BMN1-17 and MN-10 by mapping the protein sequence of these antigens with overlapping synthetic peptides (Loa C C, et al. *Curr Method* 2004, 49: 385-389; Houghton R L, et al. *Transfusion* 2002 November; 42(11):1488-1496). Recombinant antigens were observed to show highly non-specific antibody binding, therefore the antigen sequences were analyzed in order to identify shorter peptide candidates.

A repeating motif in BMN1-17 was identified that had two main variants.

(SEQ ID NO: 1)
MDSDTRVLPESLDEGVPHQFSRLGHHSDMASDINDEEPSFKIGENDIIQPPWEDTAPYH

SIDDEELDNLMRLTAQETSDDHEEGNGKLNTNKSEKTERKSHDTQTPQEIYEELDNLL

RLTAQEIYEERKEGHGKPNTNKSEKAERKSHDTQTTQEICEECEEGHDKINKNKSGNA

-continued

GIKSYDTQTTQEICEECEEGHDKINKNKSGNAGIKSYDTQTPQETSDAHEEGHDKINTN

KSEKAERKSHDTQTTQEICEECEEGHDKINKNKSGNAGIKSYDTQTPQETSDAHEEEH

GNLNKNKSGKAGIKSHNTQTPLKKKDFCKEGCHGCNNKPEDNERDPSSPDDDGGCEC

GMTNHFVFDYKTTLLLKSLKTETSTHYYIAMAAIFTISLFPCMFKAF

Repeat unit alignment:

```
                                          (SEQ ID NO: 2)
KSHDTQTTQEICEECEEGHDKINKNKSGNAGI (SEQ ID NO: 3)
KSYDTQTTQEICEECEEGHDKINKNKSGNAGI (SEQ ID NO: 4)
KSYDTQTPQETSDAHEEGHDKINTNKSEKAER (SEQ ID NO: 5)
KSHDTQTTQEICEECEEGHDKINKNKSGNAGI (SEQ ID NO: 6)
KSYDTQTPQETSDAHEEEHGNLNKNKSGKAGI (SEQ ID NO: 7)
KSHNTQTPLKKKDFCKEGCHGCN-NKPEDNER
```

Two immunodominant BMN1-17 epitopes were identified

```
BMN1-17A
                                          (SEQ ID NO: 8)
GKPNTNKSEKAERKSHDTQTTQEICEECEEGHDKINKNKSGNAGI
and BMN1-17B
                                          (SEQ ID NO: 9)
KSYDTQTPQETSDAHEEGHDKINTNKSEKAER.
```

Said epitopes may be modified to yield:

```
                                          (SEQ ID NO: 39)
Biotin-PEG(4)-GKPNTNKSEKAERKSHDTQTTQEICEECEEGH

DKINKNKSGNAGI (SEQ ID NO: 40)
Biotin-PEG(4)-KSYDTQTPQETSDAHEEGHDKINTNKSEKAER
```

A further modification of said peptide sequence to enhance stability may comprise the substitution of serine for cysteine, resulting in the sequences:

```
                                          (SEQ ID NO: 43)
GKPNTNKSEKAERKSHDTQTTQEISEESEEGHDKINKNKSGNAGI (SEQ ID NO: 44)
HQEQNNANDRSNPTGAGGQPNNESKKKAVK (SEQ ID NO: 45)
Biotin-PEG(4)-GKPNTNKSEKAERKSHDTQTTQEISEESEEGHDKI

NKNKSGNAGI (SEQ ID NO: 46)
Biotin-PEG(4)-HQEQNNANDRSNPTGAGGQPNNESKKKAVK
```

Such a modification, or any modification to enhance stability, solubility, reactivity, sensitivity, and specificity, may be utilized on any of the peptides isolated or derived from clones of the *Babesia* BMN1 family of the present invention.

In addition to the peptides described above, the present invention features *Babesia* antigen peptides derived from BMN1-9. The three available cloned sequences for BMN1-9 have differences in their amino- and carboxyl-termini, but share a core homology of 215 amino acids. In order to identify peptide antigen candidates, a library of peptides each 15 amino acids in length, overlapping by 8 amino acids, corresponding to the core homology BMN1-9 sequence was generated and analyzed.

BMN1-9 Core Homology Region:

```
                                          (SEQ ID NO: 10)
HQEQNNANDRCNPTGAGGQPNNESKKKAVKLDLDLMKETKNVCTTVNTK

LVGKAKSKLNKLEGESHKEYVAEKTKEIDEKNKKFNENLVKIEKKKKIK

VPADTGAEVDAVDDGVAGALSDLSSDISAIKTLTDDVSEKVSENLKDDE

ASATEHTDIKEKATLLQESCNGIGTILDKLAEYLNNDTTQNIKKEFDER

KKNLTSLKTKVENKDEDYV
```

Peptide Library:

```
                                          (SEQ ID NO: 11)
HQEQNNANDRCNPT (SEQ ID NO: 12)
DRCNPTGAGGQPNN (SEQ ID NO: 13)
GGQPNNESKKKAVK (SEQ ID NO: 14)
KKKAVKLDLDLMKE (SEQ ID NO: 15)
LDLMKETKNVCTTV (SEQ ID NO: 16)
NVCTTVNTKLVGKA (SEQ ID NO: 17)
KLVGKAKSKLNKLE (SEQ ID NO: 18)
KLNKLEGESHKEYV (SEQ ID NO: 19)
SHKEYVAEKTKEID (SEQ ID NO: 20)
KTKEIDEKNKKFNE (SEQ ID NO: 21)
NKKFNENLVKIEKK (SEQ ID NO: 22)
VKIEKKKKIKVPAD (SEQ ID NO: 23)
IKVPADTGAEVDAV (SEQ ID NO: 24)
AEVDAVDDGVAGAL (SEQ ID NO: 25)
GVAGALSDLSSDIS
```

-continued

LSSDISAIKTLTDD (SEQ ID NO: 26)

KTLTDDVSEKVSEN (SEQ ID NO: 27)

EKVSENLKDDEASA (SEQ ID NO: 28)

DDEASATEHTDIKE (SEQ ID NO: 29)

HTDIKEKATLLQES (SEQ ID NO: 30)

TLLQESCNGIGTIL (SEQ ID NO: 31)

GIGTILDKLAEYLN (SEQ ID NO: 32)

LAEYLNNDTTQNIK (SEQ ID NO: 33)

TTQNIKKEFDERKK (SEQ ID NO: 34)

FDERKKNLTSLKTK (SEQ ID NO: 35)

TSLKTKVENKDEDYV (SEQ ID NO: 36)

Analysis of sera selectively reactive with rBMN1-9 suggested that two nonadjacent peptide stretches possessed immunodominant epitopes, BMN1-9A (HQEQNNANDRCNPTGAGGQPNNESKKKAVK (SEQ ID NO: 37)) and BMN1-9B (NKKFNENLVKIEKKKKIKVPADTGAEVDAV (SEQ ID NO: 38)). Analysis of the peptide library with a monoclonal antibody directed against BMN1-9 revealed reactivity with a sequence contained within the 9A and 9B peptides.

The Babesia antigen peptides of the present invention, while often in a native amino acid sequence may be modified to include conservative amino acid substitutions, in accordance with standard techniques. In addition, fragments of the peptides containing, for example 5, 10, 15, 20 or 25 amino acids may be used in assays described herein.

Isolated Babesia antigens peptides may comprise, for example, the amino acid sequences of SEQ ID NOs: 8 or 9, or fragments, modified forms, or combinations thereof; or SEQ ID NO: 37 or 38, or fragments, modified forms, or combinations thereof. The isolated Babesia antigens peptides of the present invention may include polypeptides having at least, but not more than 20, 10, 5, 4, 3, 2, or 1 amino acid that differs from SEQ ID NOs: 8, 9, 37, or 38. The isolated Babesia antigens peptides may comprise polypeptides having at least 80%, 90%, 95%, 96%, 97%, 98%, and 99% sequence identity with a BMN1-17 epitope, or portion thereof, e.g. a BMN1-17 epitope having the amino acid sequence of SEQ ID NOs: 8 or 9. The isolated Babesia antigens may comprise polypeptides having at least 80%, 90%, 95%, 96%, 97%, 98%, and 99% sequence identity with a BMN1-9 epitope, or portion thereof, e.g. a BMN1-9 epitope having the amino acid sequence of SEQ ID NOs: 37 or 38.

The Babesia antigen peptide may be isolated from a BMN1 clone, or synthesized chemically, or ribosomally in a cell free system, or ribosomally within a cell. Chemical synthesis of peptides may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Merrifield et al. in *J. Am. Chem. Soc.*, Volume 85, page 2149 (1964), by Houghten et al. in *Proc. Natl. Acad. Sci. USA*, Volume 82, page 5132 (1985), and by Stewart and Young in *Solid Phase Peptide Synthesis*, Pierce Chem. Co, Rockford, Ill. (1984). Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., *Curr. Opin. Biotech.* (1993): vol. 4, p 420; M. Miller, et al., *Science* (1989): vol. 246, p 1149; A. Wlodawer, et al., *Science* (1989): vol. 245, p 616; L. H. Huang, et al., *Biochemistry* (1991): vol. 30, p 7402; M. Schnolzer, et al., *Int. J. Pept. Prot. Res.* (1992): vol. 40, p 180-193; K. Rajarathnam, et al., *Science* (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., *J. Biol. Chem.* (1992): vol. 267, p 3852; L. Abrahmsen, et al., *Biochemistry* (1991): vol. 30, p 4151; T. K. Chang, et al., *Proc. Natl. Acad. Sci. USA* (1994) 91: 12544-12548; M. Schnlzer, et al., *Science* (1992): vol., 3256, p 221; and K. Akaji, et al., *Chem. Pharm. Bull.* (Tokyo) (1985) 33: 184).

Babesia antigen peptides may be achieved using in vitro translation systems. An in vitro translation systems is, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes.

Babesia antigen peptides may be chemically modified based on linkage to a water soluble polymer and capture reagent. The polymer may have a single reactive group, such as an active ester for acylation or an aldehyde for alkylation, so that the degree of polymerization may be controlled. The water soluble polymer, or mixture thereof if desired, may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. The binding reagent may be selected from the group consisting of biotin and avidin, carbohydrates and lectins, complementary nucleotide sequences, complementary peptide sequences, effector and receptor molecules, enzyme cofactors and enzymes, and enzyme inhibitors and enzymes.

The *Babesia* antigen peptides may be chemically modified with a N-terminal biotin-linked via a tetramer of polyethylene glycol as set forth in SEQ ID NOs: 39-42.

```
1) BMN1-17A:
                                         (SEQ ID NO: 39)
Biotin-PEG(4)-GKPNTNKSEKAERKSHDTQTTQEICEECEEGHDKI

NKNKSGNAGI

2) BMN1-17B
                                         (SEQ ID NO: 40)
Biotin-PEG(4)-KSYDTQTPQETSDAHEEGHDKINTNKSEKAER
```

Peptide Sequences Synthesized:

```
1) BMN1-9A
                                         (SEQ ID NO: 41)
Biotin-PEG(4)-HQEQNNANDRCNPTGAGGQPNNESKKKAVK 2) BMN1-9B
                                         (SEQ ID NO: 42)
Biotin-PEG(4)-NKKFNENLVKIEKKKKIKVPADTGAEVDAV
```

The use of biotinylated peptides offers two advantages. First, the peptides can be immobilized on streptavidin-coated plates, leaving the entire length of the peptide free in solution, thereby increasing accessibility for antibody binding and reducing artifacts due to binding of the peptide directly to the hydrophobic microplate surface. Second, is the strategy allows for multiplexing of different biotinylated peptides in a single well, thus simplifying the assay for the end user and providing the potential for greater sensitivity through combination of complementary antigenic specificities.

The modified *Babesia* antigen peptides may comprise, for example, the amino acid sequences of SEQ ID NOs: 39 or 40, or fragments, modified forms, or combinations thereof; or SEQ ID NO: 41 or 42, or fragments, modified forms, or combinations thereof. The modified *Babesia* antigen peptides may include polypeptides having at least, but not more than 20, 10, 5, 4, 3, 2, or 1 amino acid that differs from SEQ ID NOs: 39, 40, 41, or 42. The modified *Babesia* antigen peptides may comprise polypeptides having at least 80%, 90%, 95%, 96%, 97%, 98%, and 99% sequence identity with a BMN1-17 epitope, or portion thereof, e.g. a modified BMN1-17 epitope having the amino acid sequence of SEQ ID NOs: 39 or 40. The modified *Babesia* antigen peptides may comprise polypeptides having at least 80%, 90%, 95%, 96%, 97%, 98%, and 99% sequence identity with a BMN1-9 epitope, or portion thereof, e.g. a modified BMN1-9 epitope having the amino acid sequence of SEQ ID NOs: 41 or 42.

The foregoing exemplary *Babesia* antigen peptide may be chemically modified and adapted with other polymers and/or capture reagents using no more than routine experimentation.

III. Detection Assays

Provided herein are sensitive and specific ELISA assays for the detection of *Babesia* spp. in blood through measurement of anti-*Babesia* antibodies. The modified *Babesia* antigen peptides can be applied in various quantitative rapid assay formats using simple densitometric analysis of colored-reaction product formation in test zones comprising modified *Babesia* antigen peptide covalently immobilized to a solid support on capture reagents. Such assay formats, include but are not limited to, lateral flow, vertical flow, flow-through, dip-strip, passive diffusion, dot-blot assays, plate-based assays such as filter plate wells, passive diffusion, radial diffusion, microarray, microwell, and bead-filtration assays for the detection of various *Babesia* antibodies and utilizing principles of enzyme immunoassay.

Non-limiting examples of infectious protozoan parasites of the *Babesia* species that may be detected in contaminated blood, include, *Babesia bigemina*, *Babesia bovis*, *Babesia canis*, *Babesia cati*, *Babesia divergens*, *Babesia duncani*, *Babesia felis*, *Babesia gibsoni*, *Babesia herpailuri*, *Babesia jakimovi*, *Babesia major*, *Babesia microti*, *Babesia ovate*, and *Babesia pantherae*.

Clinical samples that may be tested for *Babesia* contamination include, but are not limited to blood, blood products, platelet units/collections, platelet concentrates, serum, plasma, other blood fractions, tissue, tissue extracts, urine, lymph, hydration fluid (i.e., IV hydration fluids), nutrient fluid, or imagining agents. *Babesia* present in the sample may be collected and optionally concentrated by centrifugation or filtration. Alternatively, the sample may be dried or evaporated.

In addition, medical devices, agricultural products, environmental products, and manufacturing products, including process samples, may be tested for *Babesia* contamination using the assay described herein. Non-limiting examples of medical devices that may be tested are catheters, stents, and IVs. Non-limiting examples of agricultural products include food products and the water supply. Testing of the water supply may be extended from water that is consumed by humans and other animals to water that is used in recreational facilities including swimming pools and lakes. Non-limiting examples of environmental products include machinery that is used for processing a wide array of samples and products consumed and used by humans. Non-limiting examples of manufacturing samples include sterile products and their components and intermediates that are manufactured for medical uses.

The methods and assays may contain at least one *Babesia* antigen peptides are selected from SEQ ID NO: 39, SEQ ID NO: 40, SEQ ID NO: 41, SEQ ID NO: 42, or any combination thereof. The relative stoichiometry of these peptides may be adjusted in order to maintain high sensitivity while further improving the specificity of the assay.

Assay specificity can be optimized by adjustment of assay components known to affect immunoassay performance, including blocking agents (proteins, detergents, polyvinyls), ionic strength, and pH. For peptide-based ELISAs, the synthesized *Babesia* antigens can be attached to a solid support, such as a microplate, via a biotin-streptavidin link. This can be accomplished by biotinylating the *Babesia* antigen either during synthesis or post-synthesis by attachment of biotin to a terminal cysteine residue (added during synthesis if not naturally present) using standard maleimide crosslinkers. Streptavidin can be coated on the microplate. PEGylation of the streptavidin (covalent addition of polyethylene glycol polymer, about 20 kDA MW) may substantially increase the binding density and stability of streptavidin on the microplate, with no adverse effects. In exemplary embodiments, biotin-streptavidin are used for immobilization of the peptides. The timing of each assay step can be adjusted to allow sufficient time for both the reaction kinetics and for the processing workflow needed by automated liquid handing workstations in use in blood screening laboratories.

Figure 3:
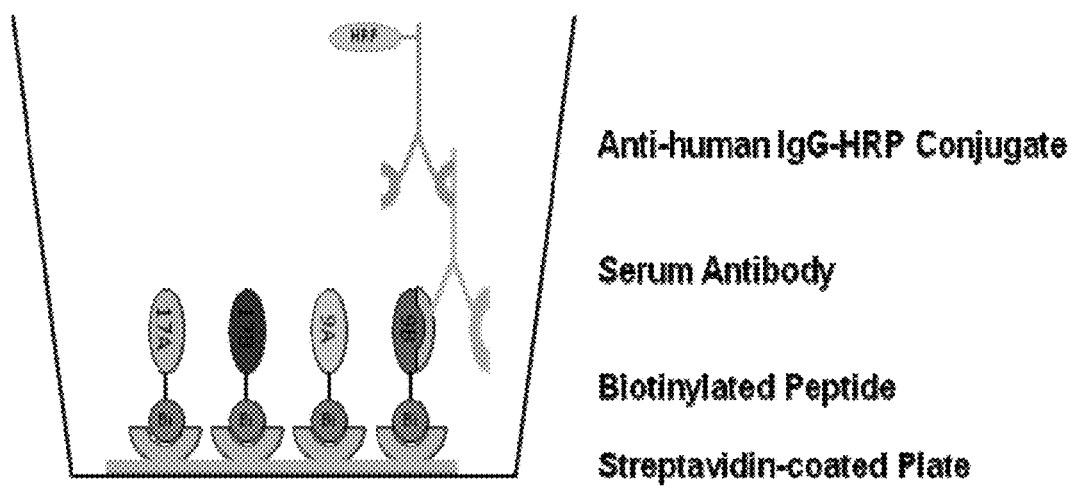
FIG. 3 is a cartoon depiction of one embodiment of the assay format. The assay is configured in a standard indirect ELISA format, in which *Babesia* antibodies in the serum sample are captured by binding to peptide antigens immobilized in the microplate well. After a washing step, detection of the bound serum antibodies is effected by incubation with a secondary antibody coupled to horseradish peroxidase (HRP) which in turn generates a colorimetric signal.

In an exemplary embodiment, the assay is configured in a standard indirect ELISA format, in which *Babesia* antibodies in the serum sample are captured by binding to peptide antigens immobilized in the microplate well. After a washing step, detection of the bound serum antibodies is effected by incubation with a secondary antibody coupled to horseradish peroxidase (HRP) which in turn generates the colorimetric signal. An important performance improvement over previous versions of this assay was achieved by biotinylating the peptide antigens and immobilizing them by binding to a streptavidin-coated microplate rather than by direct binding of antigens to the microplate (FIG. 3). This approach likely reduced steric hindrance to antibody binding and allowed greater flexibility and reproducibility in the assay.

In an alternative embodiment, the assay is configured in the QuickELISA™ format, which enables simultaneous addition of the serum sample and detection reagents to the ELISA well, followed by a single wash step and addition of enzyme substrate. The QuickELISA™ format may offer the advantages of a nearly homogeneous assay with high analytical sensitivity and specificity; however, the development time can be longer than that for a conventional indirect ELISA. The QuickELISA™ kit includes a 96-well breakaway microplate, all reagents and controls in ready-to-use format. The turnaround time for the assay is about 45 minutes from start to finish, after which results are read on a standard microplate reader. The kit detects antibodies of all isotypes in human as well as non-human species. Based on Immunetics' QuickELISA™ chemistry, it simplifies the procedure and yields higher sensitivity and specificity than conventional ELISA methods.

In certain embodiments, assay specificity may be further evaluated with samples considered to be difficult, including those with interfering substances and potentially cross-reactive disease conditions (Table 6).

TABLE 6

| Potentially Interfering substances | Potentially cross-reactive conditions |
| --- | --- |
| Autoimmune antibodies (dsDNA, anti-nuclear antibody (ANA), rheumatoid factor (RF), cytomegalovirus (VMN), heterophile antibodies, human anti-mouse antibodies (HAMA) Hypergammaglobinemia Lipemia Hypercholesterolemia Hyperpriteinemia Hemolysis Bilirubinemia pH Red blood cells White blood cells | Malaria (*Pasmodium* species) Lyme borreliosis (*Borrelia burgdorferi*) Aanaplasmosis (*Anaplasma phagocytophilum*) Toxoplasmosis (*Toxoplasma gondii*) Rocky Mountain Spotted Fever (*Rickettsia rickettsii*) Tularemia (*Francisella tularensis*) Infectious mononucleosis (EBV) Syphilis (*Treponema pallidum*) |

Assay conditions, assay reagents including wash buffer and diluents, may be adjusted to minimize the effects of interfering substances or cross-reactivity to other infectious agents.

IV. Kits

Also provided herein are kits for detecting *Babesia* spp., such as *B. microti*, in a sample. A kit for detecting *Babesia* spp. in a sample may comprise synthesized *Babesia* antigen peptides of SEQ ID NO: 39, SEQ ID NO: 40, SEQ ID NO: 41, SEQ ID NO: 42, or any combination thereof attached to streptavidin-coated microplate.

In certain embodiments, a kit for detecting *Babesia* spp. in a sample may further comprise a positive or negative *Babesia* standard, wherein the standards are obtained from non-endemic and endemic normal sera and infected sera.

In further embodiments, a kit for detecting *Babesia* in a sample may comprise an dilution solution. The kit may also comprise a wash buffer. Alternatively, the kit may provide detectable labeling-substrate dissolved in a stop buffer. In further embodiments, a kit for detecting *Babesia* spp. in a sample may still further comprise instructions for spectrophotometric detection or a color-coded scale for visual evaluation as well as sterile sample tubes for performing the reaction. Reagents in the kit may be provided in individual containers or as mixtures of one or more reagents in a single container. Any of the reagents may be provided as a liquid or as a dry powder (e.g., lyophilized).

The methods and assays of this invention may allow for the combined use of multiple antigens from the same source or genus, multiple antigens from the same species of organism, multiple antigens from different species of organisms, or any combinations thereof.

EXEMPLIFICATIONS

The invention, having been generally described, may be more readily understood by reference to the following examples, which are included merely for purposes of illustration of certain aspects and embodiments of the present invention, and are not intended to limit the invention in any way.

Example 1: Development of a Sensitive and Specific ELISA for Antibodies to *Babesia Microti* in Human Serum Background:
Human babesiosis is a tick-borne parasitic infection caused by several species of *Babesia*, including *B. microti*. The pathogen is endemic to the US Northeast and Upper Midwest. However, transfusion-transmitted infection has been documented for *B. microti* beyond the endemic region, hence the disease is a significant risk to the blood supply. Screening blood donors for *Babesia* has been proposed by the FDA and AABB, but a barrier to implementation of such a program has been the lack of an adequately sensitive and specific assay that is suitable for high-volume screening.

Methods:
We have developed an ELISA for detection of antibodies to *B. microti* based on the use of *Babesia* antigen sequences originally identified as immunodominant through phage display screening. We have identified repeat regions in several of these antigens, from which synthetic peptides and recombinant antigens were derived. ELISAs developed using these synthetic or recombinant peptides as antigens were evaluated on a panel of 43 *Babesia*-positive sera, of which all were confirmed by blood smear and 38 by IFAT, and 400 normal serum samples obtained from an area non-endemic for babesiosis.

Results:
Parallel ELISAs using synthetic or recombinant *Babesia* antigens detected 38 out of 38 IFAT-positive *Babesia* sera using a provisional cut-off. Absorbances for positive samples were >2-fold higher than the cut-off. One serum, which was blood smear-positive but IFAT-negative, was likewise negative by ELISA. Eight out of 400 normal blood donors from a non-endemic area were found reactive by ELISA (99% specificity). Further optimization of the ELISA based on refinement of antigen composition and screening of Babesia sera from clinical cases and blood donors of geographically diverse origin is underway.

Conclusion:

This ELISA shows promise as a sensitive and highly specific screening test for B. microti infection in blood donors.

Materials and Methods

Peptides: By sequence analysis, a repeat motif was identified in BMN 1-17 with two main variants. These repeat motifs were identified as putative immunodominant epitopes, and peptides corresponding to the sequences were synthesized with amino-terminal Biotin-PEG(4) derivatization. The resulting Babesia antigen peptides were named BMN1-17A (SEQ ID NO: 39) and BMN1-17B (SEQ ID NO: 40). To identify immunodominant epitopes in BMN 1-9, a peptide library was synthesized corresponding to the BMN1-9 ORF, consisting of 15-amino acid stretches with a 7 residue overlap (Mimotopes). Screening of the library revealed two candidate immunodominant sequences. These were also synthesized with amino-terminal Biotin-PEG(4) and designated BMN1-9A (SEQ ID NO: 41) and BMN1-9B (SEQ ID NO: 42).

ELISA: Wells were coated with a peptide mixture containing concentrations that had been determined to be optimal both in single-peptide/well and multi-peptide/well assays. Serum samples were diluted 1:100 in buffer, and incubated for one hour at room temperature. To detect reactive samples a monoclonal anti-human IgG-HRP conjugate (Southern Biotech) was diluted 1:10,000 and incubated for 30 min at room temperature. Substrate (TMB) and stop solution were obtained from Moss. Reactions were allowed to develop for 10 min before stopping, and absorbance read at 450 nm within 30 min of stopping. ELISA assays were first developed using individual peptides, and a final assay configuration using all 4 peptides in a single well was then optimized.

Wells were coated with 4 µg/mL streptavidin followed by a peptide mixture containing 250 ng/mL BMN1-9A, 250 ng/mL BMN1-9B, 50 ng/mL BMN1-17A and 50 ng/mL BMN1-17B. These concentrations had been determined to be optimal both in single-peptide/well and multi-peptide/well assays. Serum samples were diluted 1:100 in buffer, supplemented with 300 nM PEG-biotin to block free biotin-binding sites in the wells, and incubated for one hour at room temperature. To detect reactive samples a monoclonal anti-human IgG-HRP conjugate (Southern Biotech) was diluted 1:10,000 and incubated for 30 min at room temperature. Substrate (TMB) and stop solution were obtained from Moss. Reactions were allowed to develop for 10 min before stopping, and absorbance read at 450 nm within 30 min of stopping. ELISA assays were first developed using individual peptides, and a final assay configuration using all 4 peptides in a single well was then optimized.

Assay Sensitivity and Specificity:

ELISAs were developed to characterize the BMN1-17A (SEQ ID NO:39) and BMN1-17B (SEQ ID NO:40) peptides using forty-three serum samples, which had been confirmed positive for babesiosis in the laboratories by blood smear, PCR or xenoculture. BMN1-17A reacted with 32 out of 37 sera which were positive by IFAT and confirmed by blood smear or PCR, while BMN1-17B reacted with 23 of the same sera. The combination of both peptides improved total detection by 1 out of the 37 sera, to 33 in total.

BMN1-9A (SEQ ID NO:41) reacted with 30 and BMN1-9B (SEQ ID NO:42) reacted with 29 of the 37 IFAT-positive babesiosis sera. Among non-endemic blood donor control sera, BMN1-9A and BMN1-9B reacted with 4 and 6 samples, respectively. BMN1-17A, BMN1-17B, BMN1-9A and BMN1-9B represent novel, previously unidentified immunodominant antigens within the BMN1 family.

Sensitivity Relative to IFA with Clinically Diagnosed Babesia Samples:

Individually the four peptides (BMN1-17 A and B, BMN1-9A and 9B) showed sensitivities in ELISA ranging from 76% to 92% (Table 2), but when all four peptides were combined in one assay well they yielded an overall assay sensitivity of 100% among 38 cases of babesiosis positive by IFAT and confirmed by blood smear or PCR (Table 3).

TABLE 2

Complementarity between BMN1-9 and BMN1-17 antigens

|  | 9A or 9B positive | 9A and 9B negative |
|---|---|---|
| 17A or 17B positive | 31 | 2 |
| 17A and 17B negative | 4 | 6 |

TABLE 3

ELISA vs. IFAT

| | Blood Smear or PCR Positives | |
|---|---|---|
| | IFAT Positive | IFAT Negative |
| ELISA Positive | 38 | 0 |
| ELISA Negative | 0 | 5 |

Specificity with Donors from a Non-Endemic Region.

Four hundred control serum and plasma samples were obtained from freshly collected from young blood donors living in Arizona and the southwest—regions of the U.S. known areas non-endemic for Babesia—and based on age have lower probability of travel history outside the non-endemic region. The BMN1-17A and BMN1-17B peptides were shown to be highly specific in this group; only 3 and 2 samples were found reactive by ELISA with BMN1-17A and BMN1-17B peptides, respectively. BMN1-9A and BMN1-9B reacted with 4 and 6 samples, respectively, from this same group.

The specificity in blood donor sera from a non-endemic area ranged from 98.5% to 99.5% for individual peptides, and 98% for the combined assay (Table 4), although this value could be raised to 99% by modification of the cut-off (see below). The data obtained with the combined-peptide assay represented a performance improvement (specificity of 98% rather than 97%) relative to the results shown in the rows depicting the single BMN1-17A, BMN1-17B, BMN1-9A and BMN1-9B, where the four peptides were assayed individually and the results mathematically combined as a prototype assay.

TABLE 4

Reactivity of ELISA antigens with 400 donor sera from a non-endemic area

| Antigen | reactive | nonreactive |
|---|---|---|
| BMN1-17A | 3 | 397 |
| BMN1-17B | 2 | 398 |

TABLE 4-continued

Reactivity of ELISA antigens with 400
donor sera from a non-endemic area

| Antigen | reactive | nonreactive |
|---|---|---|
| BMN1-9A | 4 | 396 |
| BMN1-9B | 6 | 394 |
| Pooled peptide data (97% specificity) | 12 | 388 |

TABLE 4-continued

Reactivity of ELISA antigens with 400
donor sera from a non-endemic area

| Antigen | reactive | nonreactive |
|---|---|---|
| Four peptides in single well (98% specificity) | 8 | 392 |

Specificity with Donors from an Endemic Region:

An additional 200 sera were obtained from blood donors in Rhode Island, an area endemic for babesiosis. Specificity for blood donors in this area was lower, as expected, at 95.5% (Table 5); of the 9 reactive samples in this set, 6 were positive by IFAT, likely due to the inclusion of asymptomatic individuals with a history of prior exposure or infection. As these were unlinked sera from healthy donors, there was no information on possible prior exposure to B. microti or subclinical infection, both of which may be expected in an endemic donor population and would contribute to a higher background rate of serological positivity. The data shown in Table 5 were reported as a combination of results from separate assays with the four peptides. The above specificity values were based on a provisional cut-off and may be adjusted based on selection of the cut-off algorithm.

TABLE 5

Reactivity of ELISA antigens with blood
donor sera from an endemic area

| Antigen | reactive | nonreactive |
|---|---|---|
| BMN1-17A/B | 8 | 192 |
| BMN1-9A/B | 9 | 191 |
| Pooled peptide data | 9 | 191 |

Assay Cut-Off Determination:

The distribution of absorbances for samples tested in the assay containing all 4 peptides combined were reported in FIG. 1. The confirmed Babesia-positive samples showed absorbances greater than 1.0 for at least one of the 4 peptides. In contrast, the majority of control samples (from non-endemic areas) showed absorbances less than 0.1, and, except for eight samples, less than 0.53 OD; thus, a provisional cutoff of 0.53 would yield a specificity of 98%. Among donors in an area endemic for the parasite, a specificity of 95% was still observed with the same cutoff.

Six of the positives in this group were also positive by IFAT, which was in agreement with reports of seroprevalence of ~1-2% in endemic areas. Some of the remaining positives may represent incipient infections; at early stages of infection the immune response was not necessarily strong enough to be detected by serological methods.

Figure 2:
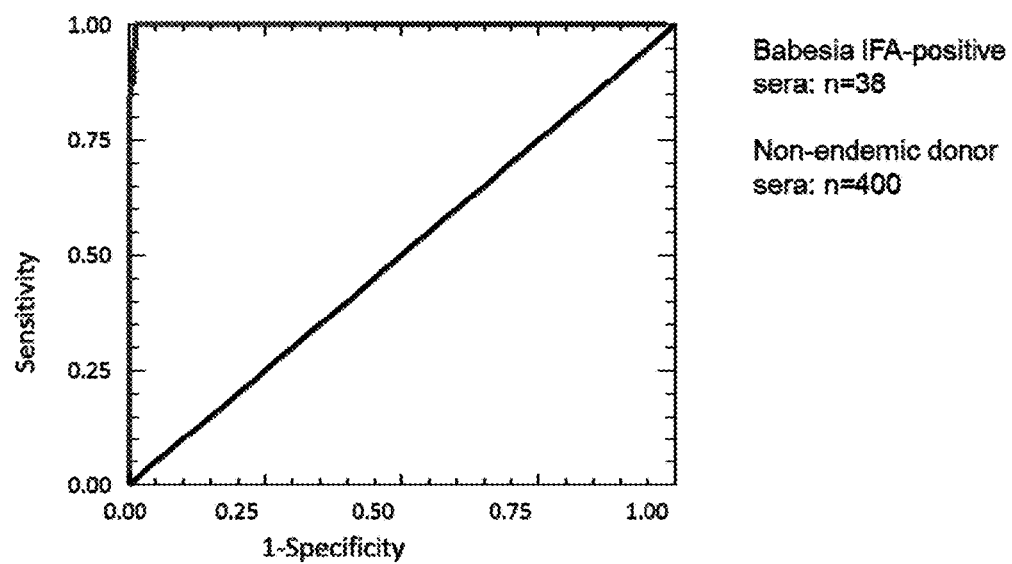
FIG. 2 is a graph demonstrating Receiver Operating Characteristic (ROC) analysis for *Babesia* peptide Enzyme-Linked Immunoabsorbent Assay (ELISA) using the four *Babesia* antigen peptides, BMN1-17A, BMN1-17B, BMN1-9A, and BMN1-9B, indicating 100% sensitivity for confirmed infections and 98% specificity at a cutoff value of 0.53.

A ROC analysis for the four-peptide combined assay indicated 100% sensitivity for confirmed infections and 98% specificity at a cutoff value of 0.53 (FIG. 2 and Table 7).

TABLE 7

ROC analysis for Babesia peptide ELISA

| Cutoff Value | Sensitivity | Specificity | Likelihood Ratio | Prev. =0.09 PPV | NPV | Prev. =0.01 PPV | NPV |
|---|---|---|---|---|---|---|---|
| 0.462 | 1.00000 | 0.97750 | 44.44444 | 0.80851 | 1.00000 | 0.30984 | 1.00000 |
| 0.528 | 1.00000 | 0.98000 | 50.00000 | 0.82609 | 1.00000 | 0.33557 | 1.00000 |
| 0.644 | 1.00000 | 0.98500 | 66.66667 | 0.86364 | 1.00000 | 0.40241 | 1.00000 |
| 0.842 | 1.00000 | 0.98750 | 80.00000 | 0.88372 | 1.00000 | 0.44693 | 1.00000 |
| 1.043 | 1.00000 | 0.99000 | 100.00000 | 0.90476 | 1.00000 | 0.50251 | 1.00000 |
| 1.254 | 0.97368 | 0.99000 | 97.36842 | 0.90244 | 0.99748 | 0.49585 | 0.99973 |

A specificity of 99% (95% Confidence Interval 97.5-99.7%) can be achieved at a cutoff value of 1.04 with no sacrifice in sensitivity, but a lower cut-off would be more appropriate for the performance range of most colorimetric assays. Modification of assay signal strength by adjustment of reagent concentrations or incubation conditions may allow a slightly lower cut-off, within the absorbance range typical for such ELISA assays, while preserving the clear distinction between positives and negatives—thereby making possible final assay operation at close to 100% sensitivity and 99% specificity. Performance values for the assay with greater statistical accuracy may be determined by testing larger numbers of both positive and negative sera.

Figure 4:
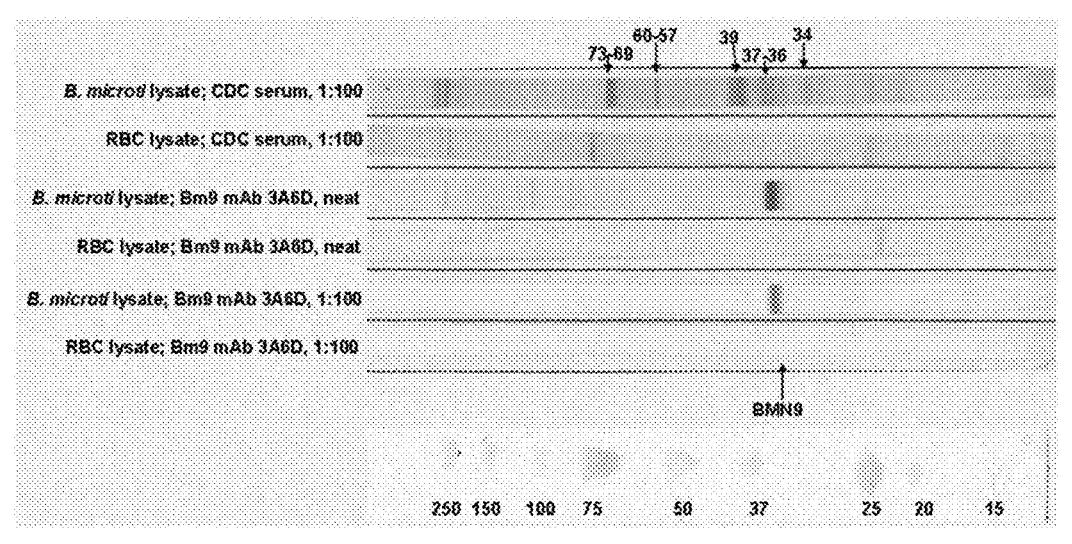

A Western blot for antibodies to B. microti based on a lysate of B. microti G1 strain was previously developed, but the identity of individual antigens had not been characterized. Ten to twelve reactive bands with molecular weights ranging from 30-150 kDa were seen, with varying band patterns in individual serum samples. As shown in FIG. 4, patient sera from the Upper Midwest and New England detect proteins that are (1) unique to the parasite lysate and (2) not reactive with normal human serum. Bands (p 36-37) may relate to BMN1-9 by virtue of its co-migration with the band detected on the same lysate with a monoclonal antibody specific for BMN1-9 (provided by Dr. Jeffrey Priest, CDC). The reactivity of an MO-1 (B. divergens) patient serum with individual bands in the B. microti lysate suggests that further characterization of antigens may yield a more pan-reactive serodiagnostic assay.

Summary of Results:

Forty-three serum samples from patients with babesiosis confirmed by blood smear, PCR or xenodiagnoses were obtained. Of these, five were seronegative, as determined by IFAT. As expected, these samples are also negative by ELISA. Of the 38 seropositive samples, all were detected by our multi-peptide ELISA assay (FIG. 1 and Table 3). Thirty-one of the 38 samples reacted with peptides from both BMN 1-17 and BMN 1-9. Two samples were reactive solely with BMN 1-17, and 5 of the samples were reactive solely with BMN 1-9, suggesting the antigens show a certain degree of complementarity (Table 2).

Among normal donors from a non-endemic area, reactivity was observed in 8 of 400 samples in a format containing four peptides in a single well (FIG. 1 and Table 4). ROC analysis was conducted to evaluate assay performance for the purpose of determining sensitivity and specificity (FIG. 2 and Table 7). Sensitivity was 100% for confirmed babesiosis cases, and among normal donors, 99% specificity was attained with no loss of sensitivity. The ROC analysis in FIG. 2 indicated that with further optimization, an assay cutoff could be selected that results in assay specificity and sensitivity both >99.

Conclusions:

Sensitivity for seropositive babesiosis cases was 100%. Specificity with normal donor sera from a non-endemic area was ≥99%. This assay of the present invention was simpler than existing assays for babesiosis (IFA, blood smear), can be performed using techniques and equipment common in most testing laboratories, and could be adapted to high throughput applications.

Example 2: Sensitive and Specific Peptide Based ELISA for Detection of Antibodies to Babesia Microti Background:

Human babesiosis is a tick-borne parasitic infection caused by several species of *Babesia*, the most common of which is *Babesia microti*. *B. microti* is endemic to the US Northeast and Upper Midwest. The FDA's annual report on blood product deviations described eight cases of transfusion-transmitted babesiosis in 2011, indicating that *B. microti*-contaminated donor blood is a significant threat to the blood supply. Screening blood donors for *Babesia* has been under discussion by the FDA and the AABB. A barrier to implementation of such screening has been the lack of a sensitive and specific assay that is suitable for high-volume screening. No licensed tests are currently commercially available.

Methods:

We have developed a peptide-based microwell ELISA for detection of antibodies to *B. microti*, based on the use of *Babesia* antigen sequences originally identified as immunodominant through phage display screening. Four immunodominant peptides have been identified from sequence analysis and epitope scanning experiments using peptide mini-libraries. The four peptides represent different sequence variants within the BMN1 gene family. A single-well ELISA incorporating all four of these peptides has been developed and validated. ELISA sensitivity was tested on a serum panel of human serum samples from 74 *Babesia*-infected study subjects, all of whom were confirmed to have had active *Babesia microti* infection by blood smear or PCR. 72 samples in this panel were seropositive by the indirect Immunofluorescence Assay (IFA) based on a cut-off titer of 1:64. Specificity of the *B. microti* ELISA was assessed on 1000 serum samples obtained from blood donors living in an area non-endemic for babesiosis (Arizona) and on 950 serum samples from blood donors living in a babesiosis-endemic region (southeastern New England).

Results:

The single-well tetra-peptide ELISA successfully recognized 69 out of 72 IFA-positive babesiosis patient sera using a provisional assay cut-off of 0.300. The assay was non-reactive with 99.5% of blood donors from non-endemic regions, and 99.1% of blood donors from southeastern New England, a *Babesia microti*-endemic region.

Conclusion:

This ELISA shows promise as a sensitive and highly specific screening test for *B. microti* infection in blood donors, as well as for detection of *B. microti* antibodies to aid in the clinical diagnosis of babesiosis.

Materials and Methods

Peptides:

BMN1-17 and BMN1-9 are two members of the BMN1 gene family that have previously been identified as immunodominant by phage display screening 1-3. Two peptides, 17A and 17B, were identified by sequence analysis as the main variant repeat motifs from BMN1-17, and were also previously identified as putative immunodominant epitopes 4,5. Peptides 9A and 9B were identified based on screening a peptide library corresponding to the BMN1-9 ORF with patient sera 5.

ELISA:

Microplate wells were coated with a peptide mixture containing concentrations that had been determined to be optimal both in single-peptide/well and multi-peptide/well assays. Serum samples were diluted 1:100 in buffer, and incubated in wells for one hour at room temperature. Bound antibodies were detected using a cocktail containing a monoclonal anti-human IgG-HRP conjugate and a monoclonal anti-human IgM-HRP conjugate (both from Southern Biotech), each diluted 1:20,000 and incubated for one hour at room temperature. Wells were incubated with HRP substrate (TMB, Moss) for 10 min before stopping, and absorbance read at 450 nm within 30 min of stopping. A provisional cut-off of 0.3 absorbance units was applied to interpret results. This cut-off value was derived from the mean ELISA absorbance among 200 non-endemic donors plus 5 standard deviations. The non-endemic donors were included in the group shown in FIG. 1.

IFA:

Slides and reagents for performing IFA to detect seroreactivity to *Babesia microti* were purchased from Fuller Laboratories (Fullerton, Calif.) and used in accordance with the manufacturer's recommended protocol. Samples were scored as positive if the observed titer was ≥1:64.

TABLE 8

ELISA Performance versus IFA on Babesiosis Patient Sera

| | | IFA (1:64) | | IFA (1:128) | | IFA (1:256) | |
|---|---|---|---|---|---|---|---|
| | | Positive | Negative | Positive | Negative | Positive | Negative |
| ELISA | Positive | 69 | 0 | 66 | 3 | 65 | 4 |
| | Negative | 3 | 2 | 1 | 4 | 1 | 4 |

TABLE 9

Figure 7:
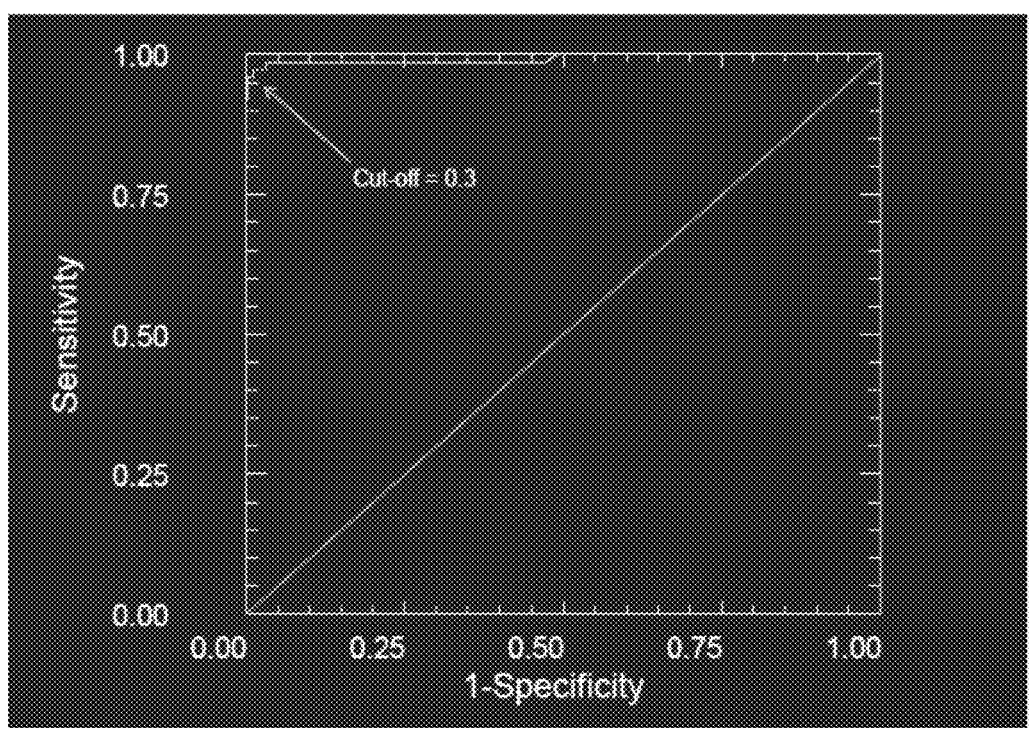
FIG. 7 is a graph demonstrating Receiver Operating Characteristic (ROC) Curve of *Babesia microti* ELISA. The data for the *Babesia* peptide ELISA containing BMN1-17A, BMN1-17B, BMN1-9A, and BMN1-9B, performed on the donor pools presented in FIG. 5, was subjected to ROC analysis. At an assay cutoff of 0.3 we observe 99.5% specificity and 95.8% sensitivity.

ROC analysis of ELISA data indicates that a specificity up to 99.8% in a non-endemic donor population can be achieved at a sensitivity of 95.8% vs. IFA at 1:64 cut-off (FIG. 7).

| Cutoff Value | Count TP A | Count FP B | Count FN C | Count TN D | Sensitivity A/(A + C) | Specificity D/(B + D) |
|---|---|---|---|---|---|---|
| 0.256 | 69 | 10 | 3 | 993 | 0.95833 | 0.99003 |
| 0.291 | 69 | 6 | 3 | 997 | 0.95833 | 0.99402 |
| 0.356 | 69 | 2 | 3 | 1001 | 0.95833 | 0.99801 |
| 0.451 | 69 | 1 | 6 | 1002 | 0.91667 | 0.99900 |

Figure 5:
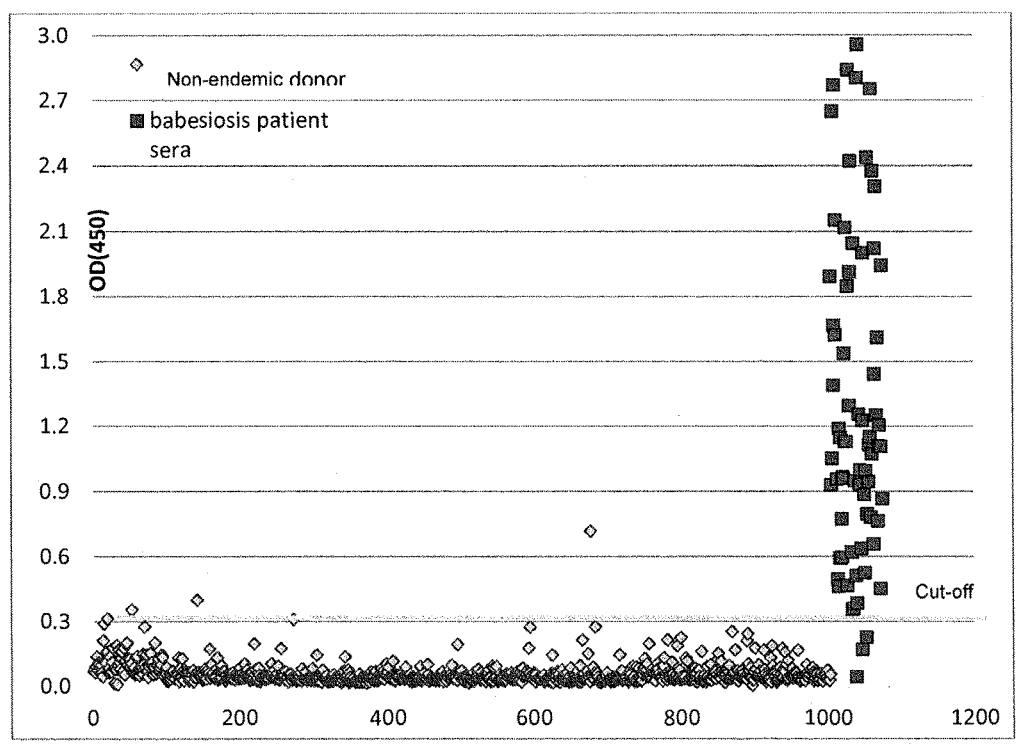
FIG. 5 shows a graph of ELISA Absorbance Values for Non-Endemic Donor Sera (1-1000) and IFA-Positive Babesiosis Patient Sera (1001-1072) using *Babesia* antigen peptides, BMN1-17A, BMN1-17B, BMN1-9A, and BMN1-9B, combined. 1000 non-endemic normal donor sera and 72 confirmed (sero-reactive by IFA) babesiosis patient sera were tested on an ELISA containing peptides BMN1-17A, BMN1-17B, BMN1-9A, and BMN1-9B with conditions optimized for performance. As a result, we observe a cutoff value of 0.3, with a specificity of 99.5%, an improvement over the previous iteration of the assay presented in FIG. 1.
Figure 6:
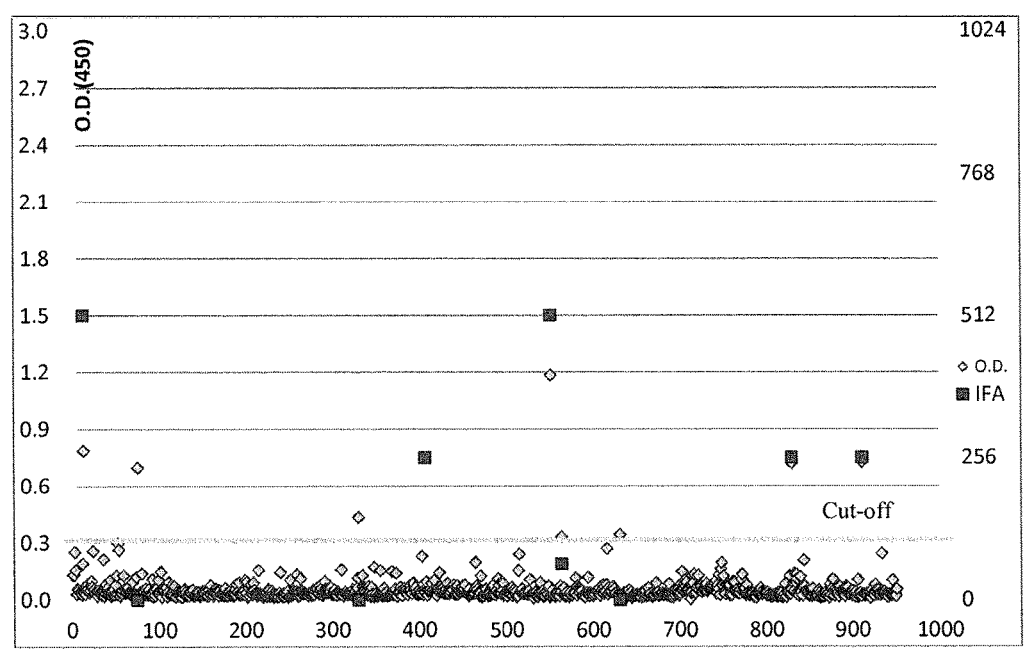
FIG. 6 depicts a graph of FIG. 2: ELISA Values for Endemic Donor Sera vs. IFA. IFA performed on samples with ELISA absorbance >0.300. 975 normal donor sera from an area endemic for babesiosis were tested using the same ELISA assay presented in FIG. 5. Reactivity among this donor population was 0.9% (9 samples). Of those samples that were reactive by ELISA, 6 were also reactive by IFA.

Summary of Results:

Sixty-nine of the 74 blood smear-positive babesiosis patient samples were detected by the multi-peptide ELISA assay (Table 8 and FIG. 5). Two of the 74 babesiosis patient sera were from early, acute infections. They were seronegative both by IFA, based on a cut-off of 1:64, and by ELISA (data not shown). The ELISA sensitivity versus IFA at 1:64 cut-off was 95.8%. The ELISA sensitivity was greater than IFA at IFA cut-offs >1:64 (Table 8). The sensitivity values for ELISA versus IFA were statistically equivalent ($p>0.05$). Five of 1000 samples (0.5%) from donors living in a non-endemic area were reactive in the ELISA (FIG. 5). These samples were negative by IFA. Nine of 950 samples (0.95%) from donors living in an area endemic for babesiosis were reactive by ELISA. zSix of these 9 were also reactive by IFA (FIG. 6). Receiver Operating Characteristic (ROC) analysis of ELISA data indicates that a specificity up to 99.8% in a non-endemic donor population can be achieved at a sensitivity of 95.8% versus IFA at 1:64 cut-off (FIG. 7).

Conclusions:

Sensitivity of the *B. microti* peptide ELISA was equivalent to that of IFA in blood smear positive babesiosis patient sera. ELISA specificity in normal blood donor sera from non-endemic or endemic areas was >99%, but endemic donors exhibit a significantly higher rate of seropositivity. This microplate ELISA assay is simpler to perform than existing assays for babesiosis (IFA, blood smear), can be carried out using techniques and equipment common in most testing laboratories, generates an objectively read and quantitated result, and could readily be adapted to high throughput donor screening. Large scale studies may be carry out in pre-IND and IND trials comprising donor screening in areas of high and low endemicity, with donor follow up by serological and PCR analyses. The ELISA may be adapted to automated high-throughput systems compatible with blood screening laboratory use.

1. Lodes M J et al. Serological expression cloning of novel immunoreactive antigens of *Babesia microti*, Infect. Immun. (2000); 68(5):2783-2790.
2. Homer M J et al. A Polymorphic Multigene Family Encoding an Immunodominant Protein from *Babesia microti*, J. Clin. Microbiol. (2000); 38(1):362-368.
3. Homer M J et al. Identification and Characterization of Putative Secreted Antigens from *Babesia microti*, J. Clin. Microbiol. (2003) 41(2):723-729.
4. Houghton R L et al. Identification of *Babesia microti*-specific immunodominant epitopes and development of a peptide EIA for detection of antibodies in serum, Transfusion 2002; 42:1488-1496.
5. Erwin J L et al. Development of a sensitive and specific ELISA for antibodies to *Babesia microti* in human serum. (2011) AABB Meeting.

INCORPORATION BY REFERENCE

All publications, patents, and patent applications mentioned herein are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequence which reference an accession number correlating to an entry in a public database, such as those maintained by The Institute for Genomic Research (TIGR) on the world wide web with the extension tigr.org and or the National Center for Biotechnology Information (NCBI) on the world wide web with the extension ncbi.nlm.nih.gov.

EQUIVALENTS AND SCOPE

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

What is claimed is:

1. A method for identifying *Babesia microti* in a sample, the method comprising:
   (a) contacting the sample to a solid support immobilized with a combination of at least four isolated, synthetic *Babesia* antigen peptides comprising (a) a polypeptide consisting of the amino acid sequence set forth in SEQ ID NO: 39 or consisting of the amino acid sequence set forth in SEQ ID NO: 45; (b) a polypeptide consisting of the amino acid sequence set forth in SEQ ID NO: 40; (c) a polypeptide consisting of the amino acid sequence set forth in SEQ ID NO: 41 or consisting of the amino acid sequence set forth in SEQ ID NO: 46; and (d) a polypeptide consisting of the amino acid sequence set forth in SEQ ID NO: 42;
   wherein a *Babesia microti* antibody present in the sample binds to at least one *Babesia* antigen peptide of the combination of at least four isolated, synthetic *Babesia* antigen peptides;
   (b) contacting the bound *Babesia microti* antibody of step (a) with a detectable label linked to a reagent that binds to the bound *Babesia microti* antibody at an epitope that is different from an epitope bound by at least one *Babesia* antigen peptide of the combination of at least four isolated, synthetic *Babesia* antigen peptides;
   (c) contacting the detectable label with a substrate to form a colored-reaction product; and
   (d) detecting the formation of the colored-reaction product as an indication of the presence of one or more *Babesia microti* in the sample.

2. The method according to claim 1, further comprising a wash step after step (a).

3. The method according to claim 1, wherein the substrate is a horseradish peroxidase substrate.

4. The method according to claim 1, wherein the sample is blood or a blood product.

5. A diagnostic kit for the identification of *Babesia microti* in a sample, the kit comprising a combination of at least four isolated, synthetic *Babesia* antigen peptides selected from (a) a polypeptide consisting of the amino acid sequence set forth in SEQ ID NO: 39 or consisting of the amino acid sequence set forth in SEQ ID NO: 45; (b) a polypeptide consisting of the amino acid sequence set forth in SEQ ID NO: 40; (c) a polypeptide consisting of the amino acid sequence set forth in SEQ ID NO: 41 or consisting of the amino acid sequence set forth in SEQ ID NO: 46; and (d) a polypeptide consisting of the amino acid sequence set forth in SEQ ID NO: 42, and instructions for use.

6. The diagnostic kit according to claim 5, wherein the combination of at least four isolated, synthetic *Babesia* antigen peptides are affixed to a solid support.

7. The diagnostic kit according to claim 5, wherein the combination of at least four isolated, synthetic *Babesia* antigen peptides comprises a polypeptide consisting of the amino acid sequence set forth in SEQ ID NO: 39 conjugated to Biotin-PEG(4).

8. The diagnostic kit according to claim 5, wherein the combination of at least four isolated, synthetic *Babesia* antigen peptides comprises a polypeptide consisting of the amino acid sequence set forth in SEQ ID NO: 40 conjugated to Biotin-PEG(4).

9. The diagnostic kit according to claim 5, wherein the combination of at least four isolated, synthetic *Babesia* antigen peptides comprises a polypeptide consisting of the amino acid sequence set forth in SEQ ID NO: 41 conjugated to Biotin-PEG(4).

10. The diagnostic kit according to claim 5, wherein the combination of at least four isolated, synthetic *Babesia* antigen peptides comprises a polypeptide consisting of the amino acid sequence set forth in SEQ ID NO: 42 conjugated to Biotin-PEG(4).

11. The diagnostic kit according to claim 5, wherein the combination of at least four isolated, synthetic *Babesia* antigen peptides comprises a polypeptide consisting of the amino acid sequence set forth in SEQ ID NO: 45 conjugated to Biotin-PEG(4).

12. The diagnostic kit according to claim 5, wherein the combination of at least four isolated, synthetic *Babesia* antigen peptides comprises a polypeptide consisting of the amino acid sequence set forth in SEQ ID NO: 46 conjugated to Biotin-PEG(4).

13. The diagnostic kit according to claim 5, wherein the combination of at least four isolated, synthetic *Babesia* antigen peptides comprises polypeptides consisting of SEQ ID NO: 40, SEQ ID NO: 42, SEQ ID NO: 45, and SEQ ID NO: 46.

14. A composition comprising a combination of at least four isolated, synthetic *Babesia* antigen peptides selected from (a) a polypeptide consisting of the amino acid sequence set forth in SEQ ID NO: 39 or consisting of the amino acid sequence set forth in SEQ ID NO: 45; (b) a polypeptide consisting of the amino acid sequence set forth in SEQ ID NO: 40; (c) a polypeptide consisting of the amino acid sequence set forth in SEQ ID NO: 41 or consisting of the amino acid sequence set forth in SEQ ID NO: 46; and (d) a polypeptide consisting of the amino acid sequence set forth in SEQ ID NO: 42.

15. The composition according to claim 14, wherein the combination of at least four isolated, synthetic *Babesia* antigen peptides comprises a polypeptide consisting of the amino acid sequence set forth in SEQ ID NO: 39 conjugated to Biotin-PEG(4).

16. The composition according to claim 14, wherein the combination of at least four isolated, synthetic *Babesia* antigen peptides comprises a polypeptide consisting of the amino acid sequence set forth in SEQ ID NO: 40 conjugated to Biotin-PEG(4).

17. The composition according to claim 14, wherein the combination of at least four isolated, synthetic *Babesia* antigen peptides comprises a polypeptide consisting of the amino acid sequence set forth in SEQ ID NO: 41 conjugated to Biotin-PEG(4).

18. The composition according to claim 14, wherein the combination of at least four isolated, synthetic *Babesia* antigen peptides comprises a polypeptide consisting of the amino acid sequence set forth in SEQ ID NO: 42 conjugated to Biotin-PEG(4).

19. The composition according to claim 14, wherein the combination of at least four isolated, synthetic *Babesia* antigen peptides comprises a polypeptide consisting of the amino acid sequence set forth in SEQ ID NO: 45 conjugated to Biotin-PEG(4).

20. The composition according to claim 14, wherein the combination of at least four isolated, synthetic *Babesia* antigen peptides comprises a polypeptide consisting of the amino acid sequence set forth in SEQ ID NO: 46 conjugated to polypeptide Biotin-PEG(4).

21. The composition according to claim 14, wherein the combination of at least four isolated, synthetic *Babesia* antigen peptides comprises polypeptides consisting of SEQ ID NO: 40, SEQ ID NO: 42, SEQ ID NO: 45, and SEQ ID NO: 46.

* * * * *

SEQUENCE LISTING

```
<160> NUMBER OF SEQ ID NOS: 46

<210> SEQ ID NO 1
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Ser Asp Thr Arg Val Leu Pro Glu Ser Leu Asp Glu Gly Val
1               5                   10                  15

Pro His Gln Phe Ser Arg Leu Gly His His Ser Asp Met Ala Ser Asp
            20                  25                  30

Ile Asn Asp Glu Glu Pro Ser Phe Lys Ile Gly Glu Asn Asp Ile Ile
        35                  40                  45

Gln Pro Pro Trp Glu Asp Thr Ala Pro Tyr His Ser Ile Asp Asp Glu
    50                  55                  60

Glu Leu Asp Asn Leu Met Arg Leu Thr Ala Gln Glu Thr Ser Asp Asp
65                  70                  75                  80
```

```
His Glu Glu Gly Asn Gly Lys Leu Asn Thr Asn Lys Ser Glu Lys Thr
                85                  90                  95
Glu Arg Lys Ser His Asp Thr Gln Thr Pro Gln Glu Ile Tyr Glu Glu
                100                 105                 110
Leu Asp Asn Leu Leu Arg Leu Thr Ala Gln Glu Ile Tyr Glu Glu Arg
                115                 120                 125
Lys Glu Gly His Gly Lys Pro Asn Thr Asn Lys Ser Glu Lys Ala Glu
                130                 135                 140
Arg Lys Ser His Asp Thr Gln Thr Thr Gln Glu Ile Cys Glu Glu Cys
145                 150                 155                 160
Glu Glu Gly His Asp Lys Ile Asn Lys Asn Lys Ser Gly Asn Ala Gly
                165                 170                 175
Ile Lys Ser Tyr Asp Thr Gln Thr Thr Gln Glu Ile Cys Glu Glu Cys
                180                 185                 190
Glu Glu Gly His Asp Lys Ile Asn Lys Asn Lys Ser Gly Asn Ala Gly
                195                 200                 205
Ile Lys Ser Tyr Asp Thr Gln Thr Pro Gln Glu Thr Ser Asp Ala His
                210                 215                 220
Glu Glu Gly His Asp Lys Ile Asn Thr Asn Lys Ser Glu Lys Ala Glu
225                 230                 235                 240
Arg Lys Ser His Asp Thr Gln Thr Thr Gln Glu Ile Cys Glu Glu Cys
                245                 250                 255
Glu Glu Gly His Asp Lys Ile Asn Lys Asn Lys Ser Gly Asn Ala Gly
                260                 265                 270
Ile Lys Ser Tyr Asp Thr Gln Thr Pro Gln Glu Thr Ser Asp Ala His
                275                 280                 285
Glu Glu Glu His Gly Asn Leu Asn Lys Asn Lys Ser Gly Lys Ala Gly
                290                 295                 300
Ile Lys Ser His Asn Thr Gln Thr Pro Leu Lys Lys Lys Asp Phe Cys
305                 310                 315                 320
Lys Glu Gly Cys His Gly Cys Asn Asn Lys Pro Glu Asp Asn Glu Arg
                325                 330                 335
Asp Pro Ser Ser Pro Asp Asp Gly Gly Cys Glu Cys Gly Met Thr
                340                 345                 350
Asn His Phe Val Phe Asp Tyr Lys Thr Thr Leu Leu Leu Lys Ser Leu
                355                 360                 365
Lys Thr Glu Thr Ser Thr His Tyr Tyr Ile Ala Met Ala Ala Ile Phe
                370                 375                 380
Thr Ile Ser Leu Phe Pro Cys Met Phe Lys Ala Phe
385                 390                 395

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Ser His Asp Thr Gln Thr Thr Gln Glu Ile Cys Glu Glu Cys Glu
1               5                   10                  15
Glu Gly His Asp Lys Ile Asn Lys Asn Lys Ser Gly Asn Ala Gly Ile
                20                  25                  30
```

```
<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Ser Tyr Asp Thr Gln Thr Thr Gln Glu Ile Cys Glu Glu Cys Glu
1               5                   10                  15

Glu Gly His Asp Lys Ile Asn Lys Asn Lys Ser Gly Asn Ala Gly Ile
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Ser Tyr Asp Thr Gln Thr Pro Gln Glu Thr Ser Asp Ala His Glu
1               5                   10                  15

Glu Gly His Asp Lys Ile Asn Thr Asn Lys Ser Glu Lys Ala Glu Arg
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Ser His Asp Thr Gln Thr Thr Gln Glu Ile Cys Glu Glu Cys Glu
1               5                   10                  15

Glu Gly His Asp Lys Ile Asn Lys Asn Lys Ser Gly Asn Ala Gly Ile
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Ser Tyr Asp Thr Gln Thr Pro Gln Glu Thr Ser Asp Ala His Glu
1               5                   10                  15

Glu Glu His Gly Asn Leu Asn Lys Asn Lys Ser Gly Lys Ala Gly Ile
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Ser His Asn Thr Gln Thr Pro Leu Lys Lys Lys Asp Phe Cys Lys
```

```
                           1               5                   10                  15
                       Glu Gly Cys His Gly Cys Asn Asn Lys Pro Glu Asp Asn Glu Arg
                                       20                  25                  30

<210> SEQ ID NO 8
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Lys Pro Asn Thr Asn Lys Ser Glu Lys Ala Glu Arg Lys Ser His
1               5                   10                  15

Asp Thr Gln Thr Thr Gln Glu Ile Cys Glu Glu Cys Glu Glu Gly His
                20                  25                  30

Asp Lys Ile Asn Lys Asn Lys Ser Gly Asn Ala Gly Ile
            35                  40                  45

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Lys Ser Tyr Asp Thr Gln Thr Pro Gln Glu Thr Ser Asp Ala His Glu
1               5                   10                  15

Glu Gly His Asp Lys Ile Asn Thr Asn Lys Ser Glu Lys Ala Glu Arg
                20                  25                  30

<210> SEQ ID NO 10
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

His Gln Glu Gln Asn Asn Ala Asn Asp Arg Cys Asn Pro Thr Gly Ala
1               5                   10                  15

Gly Gly Gln Pro Asn Asn Glu Ser Lys Lys Ala Val Lys Leu Asp
                20                  25                  30

Leu Asp Leu Met Lys Glu Thr Lys Asn Val Cys Thr Thr Val Asn Thr
            35                  40                  45

Lys Leu Val Gly Lys Ala Lys Ser Lys Leu Asn Lys Leu Glu Gly Glu
    50                  55                  60

Ser His Lys Glu Tyr Val Ala Glu Lys Thr Lys Glu Ile Asp Glu Lys
65                  70                  75                  80

Asn Lys Lys Phe Asn Glu Asn Leu Val Lys Ile Glu Lys Lys Lys
                85                  90                  95

Ile Lys Val Pro Ala Asp Thr Gly Ala Glu Val Asp Ala Val Asp Asp
            100                 105                 110

Gly Val Ala Gly Ala Leu Ser Asp Leu Ser Ser Asp Ile Ser Ala Ile
        115                 120                 125

Lys Thr Leu Thr Asp Asp Val Ser Glu Lys Val Ser Glu Asn Leu Lys
    130                 135                 140
```

```
Asp Asp Glu Ala Ser Ala Thr Glu His Thr Asp Ile Lys Glu Lys Ala
145                 150                 155                 160

Thr Leu Leu Gln Glu Ser Cys Asn Gly Ile Gly Thr Ile Leu Asp Lys
                165                 170                 175

Leu Ala Glu Tyr Leu Asn Asn Asp Thr Thr Gln Asn Ile Lys Lys Glu
            180                 185                 190

Phe Asp Glu Arg Lys Lys Asn Leu Thr Ser Leu Lys Thr Lys Val Glu
        195                 200                 205

Asn Lys Asp Glu Asp Tyr Val
    210                 215

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Gln Glu Gln Asn Asn Ala Asn Asp Arg Cys Asn Pro Thr
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Cys Asn Pro Thr Gly Ala Gly Gly Gln Pro Asn Asn
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gln Pro Asn Asn Glu Ser Lys Lys Lys Ala Val Lys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Lys Lys Ala Val Lys Leu Asp Leu Asp Leu Met Lys Glu
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 15

Leu Asp Leu Met Lys Glu Thr Lys Asn Val Cys Thr Thr Val
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Val Cys Thr Thr Val Asn Thr Lys Leu Val Gly Lys Ala
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Leu Val Gly Lys Ala Lys Ser Lys Leu Asn Lys Leu Glu
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Leu Asn Lys Leu Glu Gly Glu Ser His Lys Glu Tyr Val
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser His Lys Glu Tyr Val Ala Glu Lys Thr Lys Glu Ile Asp
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Thr Lys Glu Ile Asp Glu Lys Asn Lys Lys Phe Asn Glu
1               5                   10

<210> SEQ ID NO 21

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Lys Lys Phe Asn Glu Asn Leu Val Lys Ile Glu Lys Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Lys Ile Glu Lys Lys Lys Ile Lys Val Pro Ala Asp
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Lys Val Pro Ala Asp Thr Gly Ala Glu Val Asp Ala Val
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Glu Val Asp Ala Val Asp Asp Gly Val Ala Gly Ala Leu
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Val Ala Gly Ala Leu Ser Asp Leu Ser Ser Asp Ile Ser
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Leu Ser Ser Asp Ile Ser Ala Ile Lys Thr Leu Thr Asp Asp
 1               5                  10
```

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Lys Thr Leu Thr Asp Asp Val Ser Glu Lys Val Ser Glu Asn
 1               5                  10
```

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Glu Lys Val Ser Glu Asn Leu Lys Asp Asp Glu Ala Ser Ala
 1               5                  10
```

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Asp Asp Glu Ala Ser Ala Thr Glu His Thr Asp Ile Lys Glu
 1               5                  10
```

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
His Thr Asp Ile Lys Glu Lys Ala Thr Leu Leu Gln Glu Ser
 1               5                  10
```

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Thr Leu Leu Gln Glu Ser Cys Asn Gly Ile Gly Thr Ile Leu
 1               5                  10
```

<210> SEQ ID NO 32
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 32

Gly Ile Gly Thr Ile Leu Asp Lys Leu Ala Glu Tyr Leu Asn
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Ala Glu Tyr Leu Asn Asn Asp Thr Thr Gln Asn Ile Lys
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Thr Gln Asn Ile Lys Lys Glu Phe Asp Glu Arg Lys Lys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Asp Glu Arg Lys Lys Asn Leu Thr Ser Leu Lys Thr Lys
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Ser Leu Lys Thr Lys Val Glu Asn Lys Asp Glu Asp Tyr Val
1               5                   10                  15

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

His Gln Glu Gln Asn Asn Ala Asn Asp Arg Cys Asn Pro Thr Gly Ala
1               5                   10                  15

Gly Gly Gln Pro Asn Asn Glu Ser Lys Lys Lys Ala Val Lys
```

```
                   20                  25                  30
```

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Asn Lys Lys Phe Asn Glu Asn Leu Val Lys Ile Glu Lys Lys Lys
1               5                   10                  15

Ile Lys Val Pro Ala Asp Thr Gly Ala Glu Val Asp Ala Val
            20                  25                  30
```

<210> SEQ ID NO 39
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Biotin-PEG4

<400> SEQUENCE: 39

```
Gly Lys Pro Asn Thr Asn Lys Ser Glu Lys Ala Glu Arg Lys Ser His
1               5                   10                  15

Asp Thr Gln Thr Thr Gln Glu Ile Cys Glu Glu Cys Glu Glu Gly His
            20                  25                  30

Asp Lys Ile Asn Lys Asn Lys Ser Gly Asn Ala Gly Ile
        35                  40                  45
```

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Biotin-PEG4

<400> SEQUENCE: 40

```
Lys Ser Tyr Asp Thr Gln Thr Pro Gln Glu Thr Ser Asp Ala His Glu
1               5                   10                  15

Glu Gly His Asp Lys Ile Asn Thr Asn Lys Ser Glu Lys Ala Glu Arg
            20                  25                  30
```

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Biotin-PEG4

<400> SEQUENCE: 41

```
His Gln Glu Gln Asn Asn Ala Asn Asp Arg Cys Asn Pro Thr Gly Ala
1               5                   10                  15

Gly Gly Gln Pro Asn Asn Glu Ser Lys Lys Lys Ala Val Lys
            20                  25                  30
```

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Biotin-PEG4

<400> SEQUENCE: 42

Asn Lys Lys Phe Asn Glu Asn Leu Val Lys Ile Glu Lys Lys Lys
1               5                   10                  15

Ile Lys Val Pro Ala Asp Thr Gly Ala Glu Val Asp Ala Val
            20                  25                  30

<210> SEQ ID NO 43
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Lys Pro Asn Thr Asn Lys Ser Glu Lys Ala Glu Arg Lys Ser His
1               5                   10                  15

Asp Thr Gln Thr Thr Gln Glu Ile Ser Glu Glu Ser Glu Glu Gly His
            20                  25                  30

Asp Lys Ile Asn Lys Asn Lys Ser Gly Asn Ala Gly Ile
        35                  40                  45

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

His Gln Glu Gln Asn Asn Ala Asn Asp Arg Ser Asn Pro Thr Gly Ala
1               5                   10                  15

Gly Gly Gln Pro Asn Asn Glu Ser Lys Lys Lys Ala Val Lys
            20                  25                  30

<210> SEQ ID NO 45
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Biotin-PEG4

<400> SEQUENCE: 45

Gly Lys Pro Asn Thr Asn Lys Ser Glu Lys Ala Glu Arg Lys Ser His
1               5                   10                  15

Asp Thr Gln Thr Thr Gln Glu Ile Ser Glu Glu Ser Glu Glu Gly His
            20                  25                  30

Asp Lys Ile Asn Lys Asn Lys Ser Gly Asn Ala Gly Ile
        35                  40                  45

```
<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Biotin-PEG4

<400> SEQUENCE: 46

His Gln Glu Gln Asn Asn Ala Asn Asp Arg Ser Asn Pro Thr Gly Ala
1               5                   10                  15

Gly Gly Gln Pro Asn Asn Glu Ser Lys Lys Lys Ala Val Lys
            20                  25                  30
```